(12) United States Patent
Bissonnette et al.

(10) Patent No.: US 7,140,975 B2
(45) Date of Patent: *Nov. 28, 2006

(54) GOLD CLUB HEAD WITH VARIABLE FLEXURAL STIFFNESS FOR CONTROLLED BALL FLIGHT AND TRAJECTORY

(75) Inventors: Laurent Bissonnette, Portsmouth, RI (US); Nicholas M Nardacci, Bristol, RI (US)

(73) Assignee: Acushnet Company, Fairhaven, MA (US)

( * ) Notice: Subject to any disclaimer, the term of this patent is extended or adjusted under 35 U.S.C. 154(b) by 14 days.

This patent is subject to a terminal disclaimer.

(21) Appl. No.: 11/010,873

(22) Filed: Dec. 13, 2004

(65) Prior Publication Data

US 2005/0101409 A1    May 12, 2005

Related U.S. Application Data

(60) Division of application No. 10/428,051, filed on May 1, 2003, which is a continuation-in-part of application No. 09/551,771, filed on Apr. 18, 2000, now Pat. No. 6,605,007.

(51) Int. Cl.
  *A63B 53/04* (2006.01)
(52) U.S. Cl. ................. 473/329; 473/345; 473/349
(58) Field of Classification Search ........ 473/324–350, 473/290–291
See application file for complete search history.

(56) References Cited

U.S. PATENT DOCUMENTS

| | | | |
|---|---|---|---|
| 1,318,325 A | 10/1919 | Klin |
| 1,319,233 A | 10/1919 | Mattern |
| 1,467,435 A | 9/1923 | Kinnear |
| 1,525,352 A | 2/1925 | Aitken |
| 1,543,691 A | 6/1925 | Beat |
| 1,582,836 A | 4/1926 | Link |
| 1,589,363 A | 6/1926 | Butchart |
| 1,595,589 A | 8/1926 | Tyler |
| 1,605,551 A | 11/1926 | Mattern |
| 1,699,874 A | 1/1929 | Buhrke |

(Continued)

FOREIGN PATENT DOCUMENTS

CN    1114911    1/1996

(Continued)

OTHER PUBLICATIONS

Golf Digest, Sep. 1982, p. 25.

(Continued)

*Primary Examiner*—Sebastiano Passaniti
(74) *Attorney, Agent, or Firm*—Kristin D. Wheeler

(57) ABSTRACT

The present invention relates to a golf club head with a hitting face. The hitting face comprises a directional control portion, which has at least two zones with different flexural stiffness, such that when the hitting face strikes a golf ball the two zones deform differently to selectively control the direction of the flight of the golf ball. The directional control portion may comprise an upper zone and a lower zone, where the upper zone has a lower flexural stiffness. Alternatively, the lower zone has a lower flexural stiffness. On the other hand, the directional control portion may comprise a left zone and a right zone, and either the left or right zone may have a lower flexural stiffness to selectively control the lateral launch angle either to the left of right. The hitting face may further comprise a central zone disposed within the directional control zone, wherein the central zone has a flexural stiffness of at least about three times greater than the flexural stiffness of the directional control zone.

12 Claims, 13 Drawing Sheets

U.S. PATENT DOCUMENTS

| | | |
|---|---|---|
| 1,704,119 A | 3/1929 | Buhrke |
| 1,704,165 A | 3/1929 | Buhrke |
| 1,720,867 A | 7/1929 | Webster et al. |
| 2,034,936 A | 3/1936 | Barnhart |
| 2,087,685 A | 7/1937 | Hackney |
| 3,567,228 A | 3/1971 | Lynn |
| 3,571,900 A | 3/1971 | Hardesty |
| 3,625,518 A | 12/1971 | Solheim |
| 3,659,855 A | 5/1972 | Hardesty |
| 3,863,932 A | 2/1975 | Lezatte |
| 3,985,363 A | 10/1976 | Jepson et al. |
| 4,023,802 A | 5/1977 | Jepson et al. |
| 4,193,601 A | 3/1980 | Reid, Jr. et al. |
| 4,213,613 A | 7/1980 | Nygren |
| 4,214,754 A | 7/1980 | Zebelean |
| D267,965 S | 2/1983 | Kobayashi |
| 4,429,879 A | 2/1984 | Schmidt |
| 4,432,549 A | 2/1984 | Zebelean |
| 4,449,707 A | 5/1984 | Hayashi et al. |
| 4,451,041 A | 5/1984 | Hayashi et al. |
| 4,451,042 A | 5/1984 | Hayashi et al. |
| 4,465,221 A | 8/1984 | Schmidt |
| 4,471,961 A | 9/1984 | Masghati et al. |
| 4,489,945 A | 12/1984 | Kobayashi |
| 4,511,145 A | 4/1985 | Schmidt |
| 4,762,324 A | 8/1988 | Anderson |
| 4,792,140 A | 12/1988 | Yamaguchi et al. |
| 4,826,172 A | 5/1989 | Antonious |
| 4,842,243 A | 6/1989 | Butler |
| 4,913,438 A | 4/1990 | Anderson |
| 4,915,385 A | 4/1990 | Anderson |
| 4,915,386 A | 4/1990 | Antonious |
| 4,919,430 A | 4/1990 | Antonious |
| 4,919,431 A | 4/1990 | Antonious |
| 4,921,252 A | 5/1990 | Antonious |
| 4,928,965 A | 5/1990 | Yamaguchi et al. |
| 4,930,781 A | 6/1990 | Allen |
| 4,932,658 A | 6/1990 | Antonious |
| 4,955,610 A | 9/1990 | Creighton et al. |
| D312,858 S | 12/1990 | Anderson et al. |
| 5,000,454 A | 3/1991 | Soda |
| 5,024,437 A | 6/1991 | Anderson |
| 5,028,049 A | 7/1991 | McKeighen |
| 5,046,733 A | 9/1991 | Antonious |
| 5,056,705 A | 10/1991 | Wakita et al. |
| 5,060,951 A | 10/1991 | Allen |
| 5,067,715 A | 11/1991 | Schmidt et al. |
| 5,090,702 A | 2/1992 | Viste |
| 5,094,383 A | 3/1992 | Anderson et al. |
| 5,106,094 A | 4/1992 | Desbiolles et al. |
| 5,141,230 A | 8/1992 | Antonious |
| 5,163,682 A | 11/1992 | Schmidt et al. |
| 5,180,166 A | 1/1993 | Schmidt et al. |
| 5,183,255 A | 2/1993 | Antonious |
| 5,213,328 A | 5/1993 | Long et al. |
| 5,221,087 A | 6/1993 | Fenton et al. |
| 5,240,252 A | 8/1993 | Schmidt et al. |
| 5,242,167 A | 9/1993 | Antonious |
| 5,255,918 A | 10/1993 | Anderson et al. |
| 5,261,663 A | 11/1993 | Anderson |
| 5,261,664 A | 11/1993 | Anderson |
| 5,271,621 A | 12/1993 | Lo |
| 5,292,129 A | 3/1994 | Long et al. |
| 5,295,689 A | 3/1994 | Lundberg |
| 5,301,945 A | 4/1994 | Schmidt et al. |
| 5,318,300 A | 6/1994 | Schmidt et al. |
| 5,328,184 A | 7/1994 | Antonious |
| 5,344,140 A | 9/1994 | Anderson |
| 5,346,218 A | 9/1994 | Wyte |
| 5,351,958 A | 10/1994 | Helmstetter |
| 5,358,249 A | 10/1994 | Mendralla |
| 5,362,047 A | 11/1994 | Shaw et al. |
| 5,362,055 A | 11/1994 | Rennie |
| 5,390,924 A | 2/1995 | Antonious |
| 5,395,113 A | 3/1995 | Antonious |
| 5,397,126 A | 3/1995 | Allen |
| 5,401,021 A | 3/1995 | Allen |
| 5,405,136 A | 4/1995 | Hardman |
| 5,405,137 A | 4/1995 | Vincent et al. |
| 5,407,202 A | 4/1995 | Igarashi |
| RE34,925 E | 5/1995 | McKeighen |
| 5,417,419 A | 5/1995 | Anderson et al. |
| 5,417,559 A | 5/1995 | Schmidt |
| 5,423,535 A | 6/1995 | Shaw et al. |
| 5,429,357 A | 7/1995 | Kobayashi |
| 5,431,396 A | 7/1995 | Shieh |
| 5,433,440 A | 7/1995 | Lin |
| 5,447,307 A | 9/1995 | Antonious |
| 5,447,309 A | 9/1995 | Vincent |
| 5,451,056 A | 9/1995 | Manning |
| 5,460,376 A | 10/1995 | Schmidt et al. |
| 5,467,983 A | 11/1995 | Chen |
| 5,470,069 A | 11/1995 | Schmidt et al. |
| 5,474,296 A | 12/1995 | Schmidt et al. |
| 5,482,279 A | 1/1996 | Antonious |
| 5,497,993 A | 3/1996 | Shan |
| 5,505,453 A | 4/1996 | Mack |
| 5,522,593 A | 6/1996 | Kobayashi et al. |
| 5,524,331 A | 6/1996 | Pond |
| 5,533,729 A | 7/1996 | Leu |
| 5,536,006 A | 7/1996 | Shieh |
| 5,547,630 A | 8/1996 | Schmidt |
| 5,549,297 A | 8/1996 | Mahaffey |
| 5,564,994 A | 10/1996 | Chang |
| 5,584,770 A | 12/1996 | Jensen |
| 5,595,552 A | 1/1997 | Wright et al. |
| 5,611,741 A | 3/1997 | Schmidt et al. |
| 5,611,742 A | 3/1997 | Kobayashi |
| D379,393 S | 5/1997 | Kubica et al. |
| 5,626,530 A | 5/1997 | Schmidt et al. |
| 5,643,104 A | 7/1997 | Antonious |
| 5,643,108 A | 7/1997 | Cheng |
| 5,643,110 A | 7/1997 | Igarashi |
| 5,649,872 A | 7/1997 | Antonious |
| 5,651,409 A | 7/1997 | Sheehan |
| 5,655,976 A | 8/1997 | Rife |
| 5,669,827 A | 9/1997 | Nagamoto |
| 5,669,829 A | 9/1997 | Lin |
| 5,674,132 A | 10/1997 | Fisher |
| D387,113 S | 12/1997 | Burrows |
| 5,695,411 A | 12/1997 | Wright et al. |
| 5,709,614 A | 1/1998 | Horiba |
| 5,709,615 A | 1/1998 | Liang |
| 5,711,722 A | 1/1998 | Miyajima et al. |
| 5,716,292 A | 2/1998 | Huang |
| 5,718,641 A | 2/1998 | Lin |
| 5,720,673 A | 2/1998 | Anderson |
| 5,743,813 A | 4/1998 | Chen et al. |
| 5,753,170 A | 5/1998 | Muang |
| 5,755,624 A | 5/1998 | Helmstetter |
| 5,755,627 A | 5/1998 | Yamazaki et al. |
| 5,762,567 A | 6/1998 | Antonious |
| 5,766,092 A | 6/1998 | Mimeur et al. |
| 5,766,094 A | 6/1998 | Mahaffey et al. |
| 5,766,095 A | 6/1998 | Antonious |
| 5,776,011 A | 7/1998 | Su et al. |
| 5,807,190 A | 9/1998 | Krumme et al. |
| 5,827,132 A | 10/1998 | Bamber |
| RE35,955 E | 11/1998 | Lu |
| D401,652 S | 11/1998 | Burrows |
| 5,830,084 A | 11/1998 | Kosmatka |
| 5,839,975 A | 11/1998 | Lundberg |
| 5,842,934 A | 12/1998 | Ezaki et al. |
| 5,851,159 A | 12/1998 | Burrows |

| | | | | | |
|---|---|---|---|---|---|
| 5,863,261 A | 1/1999 | Eggiman | JP | 6126002 | 5/1994 |
| 5,873,791 A | 2/1999 | Allen | JP | 6154367 | 6/1994 |
| 5,873,795 A | 2/1999 | Wozny et al. | JP | 6182005 | 7/1994 |
| D406,294 S | 3/1999 | Burrows | JP | 6269518 | 9/1994 |
| 5,888,148 A | 3/1999 | Allen | JP | 8168541 | 7/1996 |
| 5,890,973 A | 4/1999 | Gamble | JP | 8243194 | 9/1996 |
| D411,272 S | 6/1999 | Burrows | JP | 8280853 | 10/1996 |
| 5,908,357 A | 6/1999 | Hsieh | JP | 8280854 | 10/1996 |
| 5,921,872 A | 7/1999 | Kobayashi | JP | 8294550 | 11/1996 |
| 5,931,746 A | 8/1999 | Soong | JP | 9028842 | 2/1997 |
| 5,935,019 A | 8/1999 | Yamamoto | JP | 9047531 | 2/1997 |
| 5,938,541 A | 8/1999 | Allen et al. | JP | 9154985 | 6/1997 |
| 5,941,782 A | 8/1999 | Cook | JP | 9168613 | 6/1997 |
| 5,944,619 A | 8/1999 | Cameron | JP | 9192270 | 7/1997 |
| 5,954,596 A | 9/1999 | Noble et al. | JP | 9192273 | 7/1997 |
| 5,961,394 A | 10/1999 | Minabe | JP | 9239074 | 9/1997 |
| 5,967,905 A | 10/1999 | Nakahara et al. | JP | 9239075 | 9/1997 |
| 5,971,868 A | 10/1999 | Kosmatka | JP | 9248353 | 9/1997 |
| 5,993,329 A | 11/1999 | Shich | JP | 2717759 | 11/1997 |
| 6,007,432 A | 12/1999 | Kosmatka | JP | 9294833 | 11/1997 |
| 6,027,416 A | 2/2000 | Schmidt et al. | JP | 9299519 | 11/1997 |
| 6,248,025 B1 | 6/2001 | Murphy | JP | 10024126 | 1/1998 |
| 6,338,683 B1 | 1/2002 | Kosmatka | JP | 10024128 | 1/1998 |
| 6,354,962 B1 | 3/2002 | Galloway | JP | 10085369 | 4/1998 |
| 6,368,234 B1 | 4/2002 | Galloway | JP | 10118227 | 5/1998 |
| 6,381,828 B1 | 5/2002 | Boyce | JP | 10137372 | 5/1998 |
| 6,390,933 B1 | 5/2002 | Galloway | JP | 10155943 | 6/1998 |
| 6,595,057 B1 | 7/2003 | Bissonnette et al. | JP | 10258142 | 9/1998 |
| 6,605,007 B1 | 8/2003 | Bissonnette et al. | JP | 10263121 | 10/1998 |
| | | | JP | 10323410 | 12/1998 |
| | | | JP | 10337347 | 12/1998 |

FOREIGN PATENT DOCUMENTS

| | | |
|---|---|---|
| GB | 2268693 A | 1/1994 |
| GB | 2331938 A | 6/1999 |
| JP | 59207169 | 11/1984 |
| JP | 61033682 | 2/1986 |
| JP | 61162967 | 7/1986 |
| JP | 61181477 | 8/1986 |
| JP | 61185281 | 8/1986 |
| JP | 61240977 | 10/1986 |
| JP | 1244770 | 9/1989 |
| JP | 02130519 | 5/1990 |
| JP | 4020357 | 1/1992 |
| JP | 4327864 | 11/1992 |
| JP | 5212526 | 8/1993 |
| JP | 05237207 | 9/1993 |
| JP | 6007487 | 1/1994 |
| JP | 06031016 | 2/1994 |
| JP | 6114126 | 4/1994 |

OTHER PUBLICATIONS

Golf Digest, Dec. 1981, p. 58-59.

"The Search for the Perfect Swing," Cochran, A.J. & Stobbs, J. Philadelphi, J.B. Lippincott, 1968.

"Science of Golf I, Proceeding of the World Scientific Congress of Golf," Ed. Cochran, A.J., E & FN Spon Publishing, 1990.

"The Physics of Golf," Jorgensen, T.P., Springer-Verlag, 1994.

"Science of Golf II, Proceedings of the World Scientific Congress of Golf," Eds. Cochran, A.J. and Farrally, M.R., E & FN Spon Publishing 1994.

"Golf: the Scientific Way," Ed. Cochran, A.J., 1995.

"How Golf Clubs Really Work and How to Optimized Their Designs" Werner, F.D. & Greig, R.C. Orgin Inc., 2000.

"Variable Face Thickness Technology," Calloway Golf advertisement, undated.

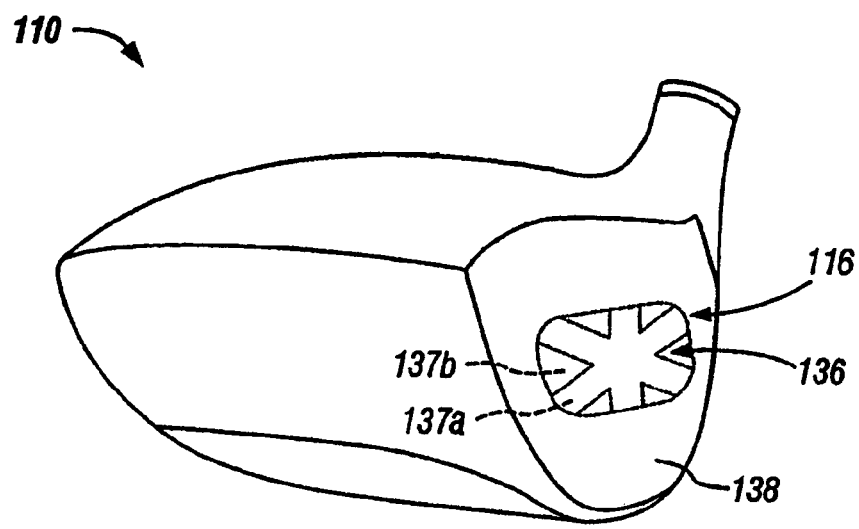
FIG. 6
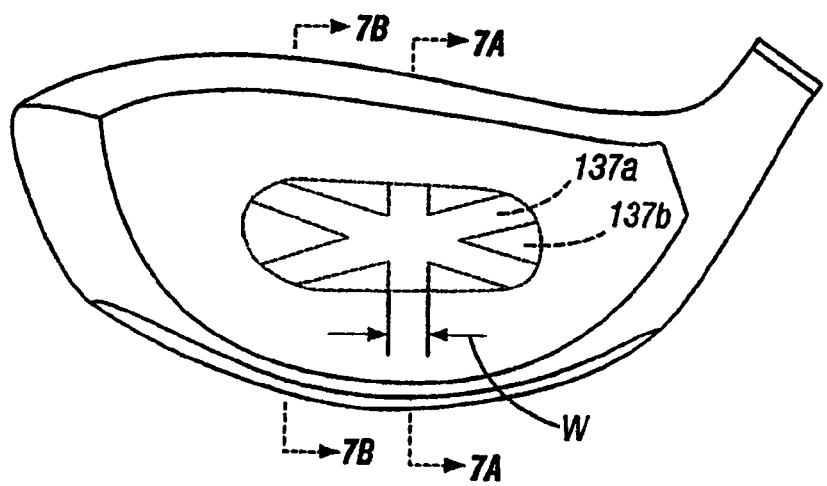
FIG. 7
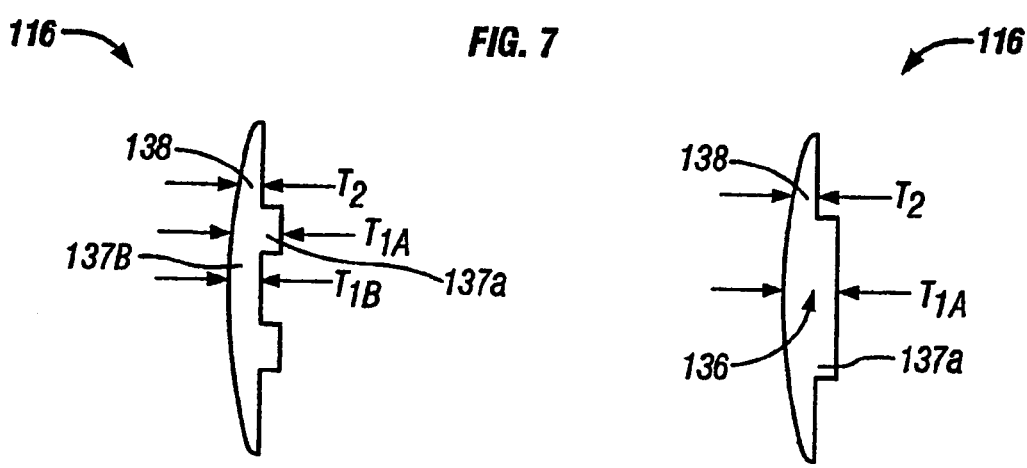
FIG. 7A          FIG. 7B

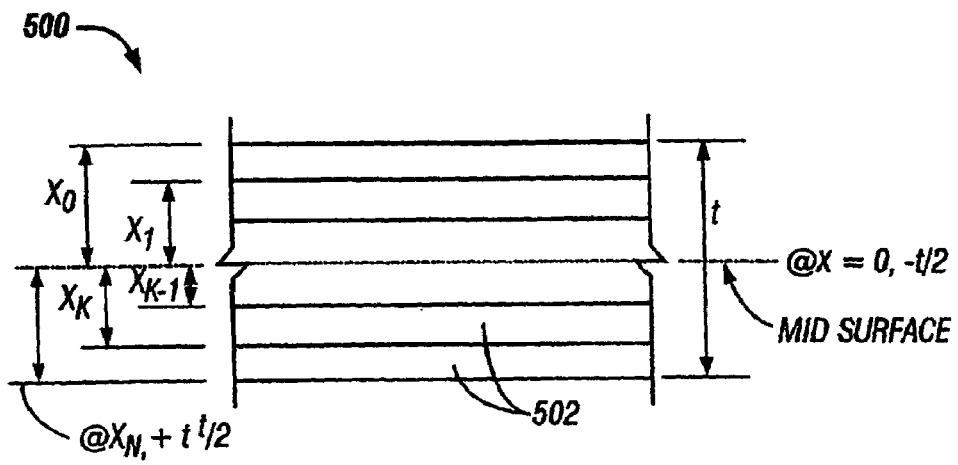
FIG. 14
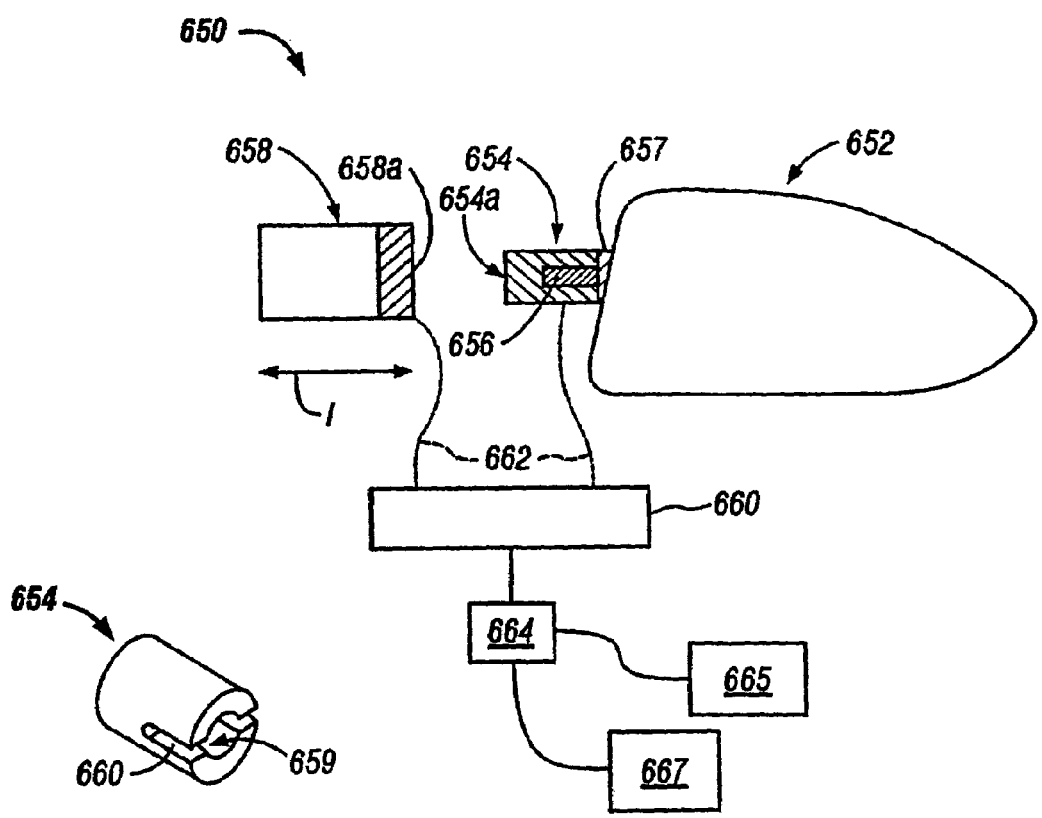
FIG. 15A  FIG. 15B

GOLD CLUB HEAD WITH VARIABLE FLEXURAL STIFFNESS FOR CONTROLLED BALL FLIGHT AND TRAJECTORY

CROSS-REFERENCE TO RELATED APPLICATION

This non-provisional utility application is a divisional application of co-pending U.S. patent application Ser. No. 10/428,051 filed on May 1, 2003, which is a continuation-in-part of U.S. patent application Ser. No. 09/551,771 filed on Apr. 18, 2000, now U.S. Pat. No. 6,605,007. The disclosure of the parent patent application and patent are incorporated herein in their entirety.

FIELD OF THE INVENTION

The invention is an improved golf club head. More particularly, the invention is a golf club head with an improved striking face having discrete zones with varying flexural stiffness, improved accuracy, and a high coefficient of restitution.

BACKGROUND OF THE INVENTION

The complexities of golf club design are well-known. The specifications for each component of the club (i.e., the club head, shaft, hosel, grip, and subcomponents thereof) directly impact the performance of the club. Thus, by varying the design specifications, a golf club can be tailored to have specific performance characteristics.

The design of club heads has long been studied. Among the more prominent considerations in club head design are loft, lie, face angle, horizontal face bulge, vertical face roll, face progression, face size, sole curvature, center of gravity, material selection, and overall head weight. While this basic set of criteria is generally the focus of golf club engineering, several other design aspects must also be addressed. The interior design of the club head may be tailored to achieve particular characteristics, such as the inclusion of hosel or shaft attachment means, perimeter weights on the face or body of the club head, and fillers within hollow club heads to improve acoustics.

Golf club heads must also be strong to withstand the repeated impacts that occur during collisions between the golf club and the ball. The loading that occurs during this transient event can accelerate the golf ball to about four orders of magnitude greater than gravity. Thus, the club face and body should be designed to resist permanent deformation or catastrophic failure by material yield or fracture. Conventional hollow metal wood drivers made from titanium typically have a uniform face thickness exceeding 0.010 inch to ensure structural integrity of the club head.

Players generally seek a metal wood driver and golf ball combination that delivers maximum distance and landing accuracy. The distance a ball travels after impact is dictated by the magnitude and direction of the ball's translational velocity and the ball's rotational velocity or spin. Environmental conditions, including atmospheric pressure, humidity, temperature, and wind speed further influence the ball's flight. However, these environmental effects are beyond the control of the golf equipment manufacturer. Golf ball landing accuracy is driven by a number of factors as well. Some of these factors are attributed to club head design, such as center of gravity, face curvature and club face flexibility.

The United States Golf Association (USGA), the governing body for the rules of golf in the United States, has specifications for the performance of golf balls. These performance specifications dictate the size and weight of a conforming golf ball. One USGA rule limits the golf ball's initial velocity after a prescribed impact to 250 feet per second±2% (or 255 feet per second maximum initial velocity). To achieve greater golf ball travel distance, ball velocity after impact must be maximized while remaining within this rule.

Generally, golf ball travel distance is a function of the total kinetic energy imparted to the ball during impact with the club head, along with associated environmental effects. During impact, kinetic energy is transferred from the club and stored as elastic strain energy in the club head and as viscoelastic strain energy in the ball. After impact, the stored energy in the ball and in the club is transformed back into kinetic energy in the form of translational and rotational velocity of the ball as well as the club. Since the collision is not perfectly elastic, a portion of energy is dissipated in club head vibration and in viscoelastic relaxation of the ball. Viscoelastic relaxation is a material property of the polymeric materials used in all manufactured golf balls.

Viscoelastic relaxation of the ball is a parasitic energy source, which is dependent upon the rate of deformation. To minimize this effect, the rate of deformation must be reduced. This may be accomplished by allowing more club face deformation during impact. Since metallic deformation may be purely elastic, the strain energy stored in the club face is returned to the ball after impact thereby increasing the ball's outbound velocity after impact.

A variety of techniques may be utilized to vary the allowable deformation of the club face, including uniform face thinning, thinned faces with ribbed stiffeners and varying thickness, among others. These designs should have sufficient structural integrity to withstand repeated impacts without permanent deformation of the club face. In general, conventional club heads also exhibit wide variations in the coefficient of restitution (COR) depending on the impact location on the face of the club. Furthermore, the accuracy of conventional clubs is highly dependent on impact location.

Thus, there is a need for a golf club head with a hitting face that maximizes golf ball travel distance while maintaining golf ball landing accuracy.

SUMMARY OF THE INVENTION

The present invention relates to a golf club head adapted for attachment to a shaft. The head includes a face and a body. The face is configured and dimensioned so that it includes a central portion and an adjacent surrounding intermediate portion. The central portion is relatively rigid and the intermediate portion is relatively flexible so that upon ball impact, the intermediate portion of the face deforms to provide high ball velocity, while the central portion is substantially un-deformed so that the ball flies on-target. Thus, upon ball impact the deformation of the intermediate portion allows the central region to move into and out of the club head as a unit. As a result, the head exhibits a coefficient of restitution greater than 0.81.

The above is accomplished by providing the central portion with a first flexural stiffness and the intermediate portion with a second flexural stiffness. Flexural stiffness is defined as Young's modulus or elastic modulus (E) times the portion's thickness (t) cubed or $Et^3$. The first flexural stiffness is substantially different from the second flexural stiffness. As a result, upon ball impact, the intermediate portion exhibits substantial deformation so that the central portion moves into the club head, and the central portion exhibits minimal deformation.

In one embodiment, the first flexural stiffness is at least three times the second flexural stiffness. In other embodiments, the first flexural stiffness is six to twelve times the second flexural stiffness. More preferably, the first flexural stiffness is greater than 25,000 lb-in. Most preferably, the first flexural stiffness is greater than 55,000 lb-in. Preferably, the second flexural stiffness is less than 16,000 lb-in. More preferably, the second flexural stiffness is less than 10,000 lb-in.

Since the flexural stiffness is a function of material and thickness, the following techniques can be used to achieve the substantial difference between the first and second flexural stiffness: 1) different materials can be used for each portion, 2) different thicknesses can be used for each portion, or 3) different materials and thicknesses can be used for each portion. For example, in one embodiment, the thickness of the central portion is greater than the thickness of the intermediate portion and the material for both portions is the same, e.g., titanium or steel.

The golf club head further includes a perimeter portion disposed between the intermediate portion and the body of the club. In one embodiment, the perimeter portion has a third flexural stiffness that is at least two times greater than the second flexural stiffness. The area of the perimeter portion preferably comprises less than 30% of the total area of the club head face.

In an alternative embodiment, a golf club head includes a shell that defines an inner cavity and a face. The face defines a face area and includes a first portion in the center and a second portion adjacent thereto. The first portion has a first thickness and defines a first area. The second portion has a second thickness. The first area is between about 15% and about 60% of the total face area, and the first thickness is greater than the second thickness. More preferably, the first area is between about 20% and 50% of the face area. The shell further includes a top crown portion and a spaced-apart sole plate, a heel portion and a spaced toe portion, and a rear spaced from the face.

In the club heads discussed above, the first, second, and third portions can have various shapes, such as the shape of the face or an elliptical shape. Furthermore, the club head inner cavities can have a volume greater than about 250 cubic centimeters, and more preferably a volume greater than about 275 cubic centimeters. It is preferred that the face of the club head has a loft of less than about 13°.

In addition, the central, intermediate, and perimeter portions can each have variable thicknesses.

Another feature of the present invention is locating the center of gravity of the club head with respect to a Cartesian coordinate system. The origin of the Cartesian coordinate system preferably coincides with the geometric center of the hitting face. The X-axis is a horizontal axis positioned tangent to the geometric center of the hitting face with the positive direction toward the heel of the club. The Y-axis is another horizontal axis orthogonal to the X-axis with the positive direction toward the rear of the club. The Z-axis is a vertical axis orthogonal to both the X-axis and Y-axis with the positive direction toward the crown of the club. The center of gravity is preferably located behind and lower than the geometric center of the face.

In one embodiment, the center of gravity is spaced from the geometric center along the Z-axis by a first distance of at least about 0.1". More preferably, the center of gravity is spaced from the geometric center along the Z-axis toward the sole plate, wherein the first distance is at least about 0.15". In another embodiment, the center of gravity is spaced a second distance from the geometric center along the X-axis, wherein the second distance is less than about 0.02". In addition, the center of gravity is spaced a third distance from the geometric center along the Y-axis toward the rear portion, wherein the third distance is less than about 1.25".

The present invention is also directed to a golf club head having a hitting face and adapted for attachment to a shaft. The face includes a total face area and first primary resonant frequency, which is preferably less than about 2900 Hz. The face further includes a central zone that includes a geometric center of the face, and an intermediate zone disposed adjacent the central zone. The central zone has a first flexural stiffness and a central zone area that is at least 15% of the total face area. The intermediate zone has a second flexural stiffness. The first flexural stiffness is at least 25,000 lb-in and greater than the second flexural stiffness.

An embodiment of the present invention is directed to a golf club head adapted for attachment to a shaft and having a hitting face, wherein the hitting face comprises a directional control portion, said directional controlled portion comprises two or more zones having different flexural stiffness, such that when the hitting face impacts a golf ball the zones exhibit different degrees of deformation to selectively control the direction of the flight of the golf ball. The hitting face may further include a central portion disposed within the directional control portion, which contains a geometric center of the hitting face, and the flexural stiffness of the central portion is at least about three times, preferably at least about six times and more preferably at least about twelve times, greater than the flexural stiffness of the directional control portion.

The golf club head may further have a perimeter portion disposed around the directional control portion, wherein the flexural stiffness of the perimeter portion is at least about two times greater than the flexural stiffness of the directional control portion. In accordance to one aspect, the flexural stiffness of a first zone of said two or more directional control zones is between about 8,500 lb-in to about 60,000 lb-in. The flexural stiffness of a second zone of said two or more zones is about 0.5 time to about two times the flexural stiffness of the first zone. Furthermore, the flexural stiffness of a third zone of said two or more zones is about 0.7 times to about 1.3 times the flexural stiffness of the first zone, and the flexural stiffness of a fourth zone of said two or more zones is about 0.7 times to about two times the flexural stiffness of the first zone.

The directional control portion may comprise an upper crown zone and a lower heel zone, or may comprise a lateral heel zone and a lateral toe zone. Alternatively, the directional control portion may comprise all four of these zones. Preferably, these four zones are delineated by a vertical center line and a horizontal center line of the hitting face.

BRIEF DESCRIPTION OF THE DRAWINGS

Preferred features of the present invention are disclosed in the accompanying drawings, wherein similar reference characters denote similar elements throughout the several views, and wherein:

FIG. 6 is a toe side, front, and perspective view of a second embodiment of a golf club head of the present invention;

FIG. 7 is a front, elevational view of the golf club head of FIG. 6;

FIG. 7A is a cross-sectional view of the face of the golf club head of FIG. 7 along line 7A—7A;

FIG. 7B shows a cross-sectional view the face of the golf club head of FIG. 7 along line 7B—7B;

FIG. 14 is an enlarged, elevational view of a portion of the face of a laminated golf club head of the present invention;

FIG. 15 is a schematic representation of a testing apparatus for obtaining frequency response data from a club head;

FIG. 15A is a perspective view of an attached mass for use with the testing apparatus of FIG. 15;

DETAILED DESCRIPTION OF THE PREFERRED EMBODIMENT

Figure 5:
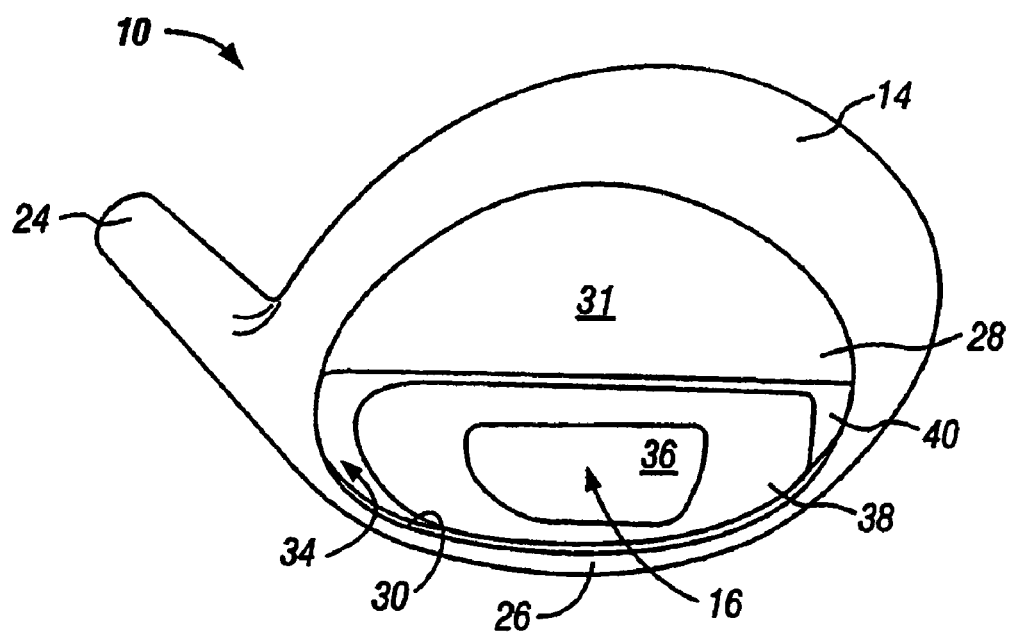
FIG. 5 is a bottom, perspective view of the golf club head of FIG. 1.

Referring to FIGS. 1–5, a first embodiment of a golf club head 10 of the present invention is shown. Club head 10 includes shell 12 with body 14, hitting face 16, toe portion 18, heel portion 20, sole plate 22, hosel 24, bottom portion 26, crown portion 28, and rear portion 29. The sole plate 22 fits in a recess 30 (as shown in FIG. 5) in the bottom portion 26 of body 14. The shell 12 and sole plate 22 create an inner cavity 31 (as shown in FIG. 5). The hitting face 16 has an exterior surface 32 and an interior surface 34. The exterior surface 32 may optionally have grooves 35.

A golf club shaft (not shown) is attached at hosel 24 and is disposed along a shaft axis SHA. The hosel may extend to the bottom of the club head, may terminate at a location between the top and bottom portions of the head, or the hosel can terminate flush with the top portion and extend into the cavity in the head.

Inner cavity 31 of club head 10 may be empty, or alternatively may be filled with foam or other low specific gravity material. It is preferred that the inner cavity 31 has a volume greater than 250 cubic centimeters, and more preferably greater than 275 cubic centimeters. Preferably, the mass of the inventive club head is greater than 150 grams but less than 220 grams.

Figure 3:
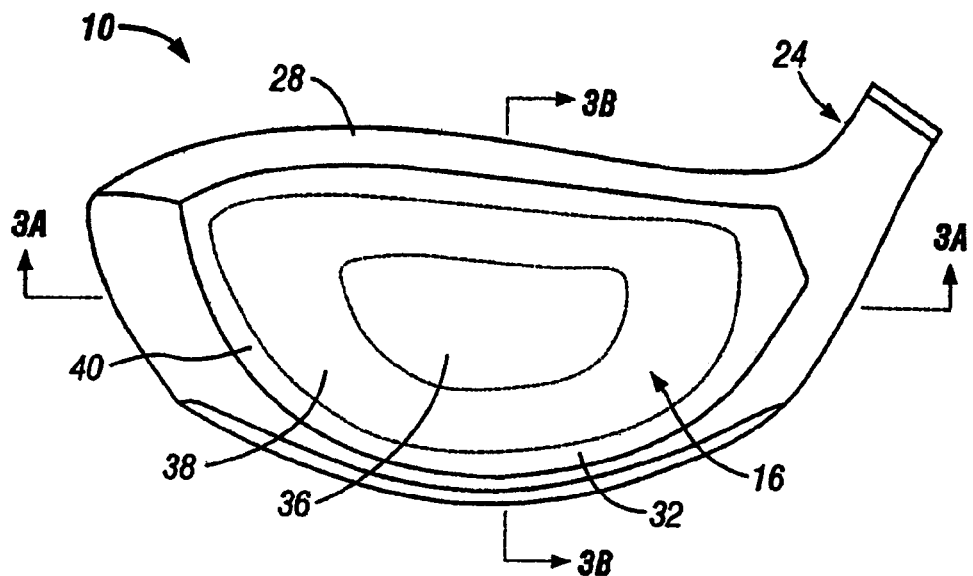
FIG. 3 is a front, elevational view of the golf club head of FIG. 1.
Figure 3A:
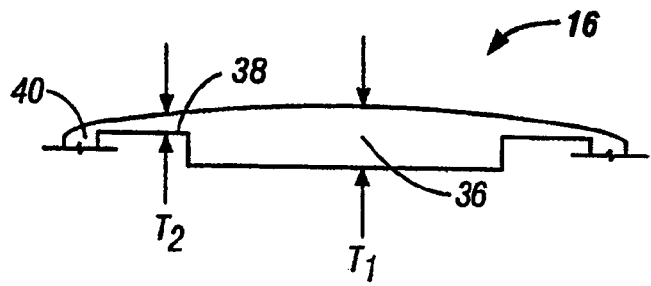
FIG. 3A is a cross-sectional view of the face of the golf club head of FIG. 3 along line 3A—3A.
Figure 3B:
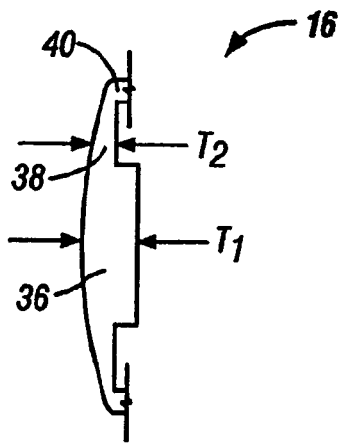
FIG. 3B shows a cross-sectional view the face of the golf club head of FIG. 3 along line 3B—3B.
Figure 4:
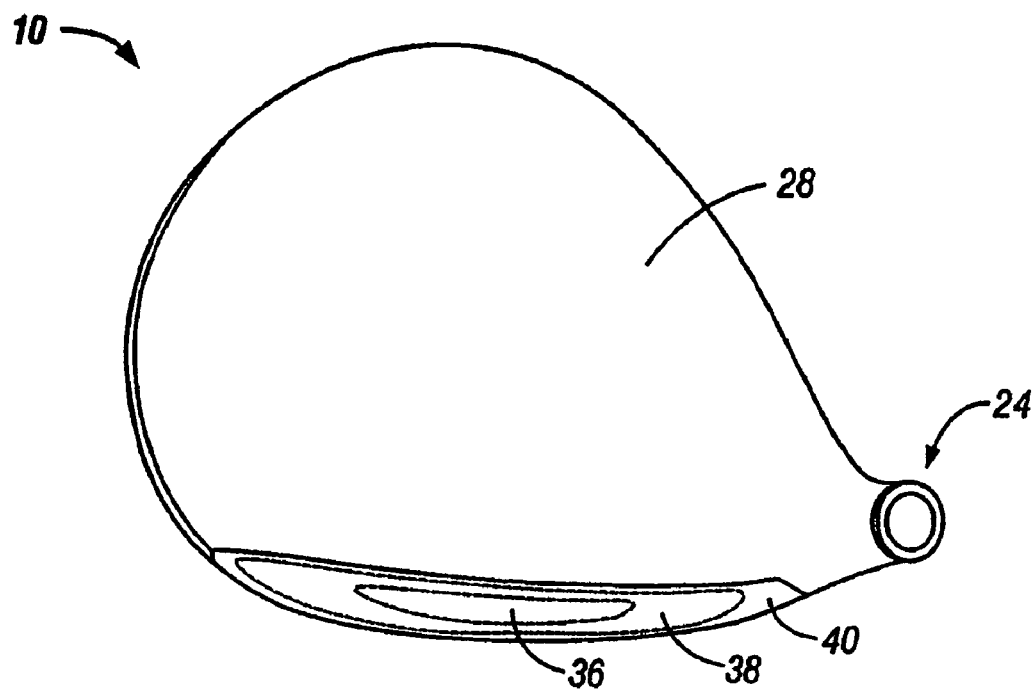
FIG. 4 is a top view of the golf club head of FIG. 1.

Referring to FIGS. 3–3B, the face 16 includes a central zone or portion 36, an intermediate zone or surrounding portion 38 adjacent the central zone 36, and an optional perimeter zone or outer portion 40. The intermediate zone 38 preferably surrounds central zone 36, and the perimeter zone 40 preferably surrounds the intermediate zone 38. The perimeter zone 40 is located between the intermediate zone 38 and crown portion 28. In the following specification and claims, the central zone 36 is a contiguous zone centrally located on the hitting face 16 and containing a geometric center ("GC") of the hitting face.

Zones 36, 38 and 40 have a shape that is similar to the shape of hitting face 16 only with a smaller area, as discussed in detail below. Preferably, zones 36, 38 and 40 are substantially concentric to each other within hitting face 16. The central zone 36 has a first thickness $t_1$. The intermediate zone 38 has a second thickness $t_2$. The first thickness $t_1$ is greater than the second thickness $t_2$. Typically, when the club head is cast, the perimeter zone 40 will be thicker than the intermediate zone 38. However, the present invention is not limited to this configuration. Preferably, the first thickness $t_1$ is equal to about one and a half (1.5) times the thickness $t_2$ to about four (4) times the thickness $t_2$ of the intermediate zone 38.

The thickness relationships between the zones 36, 38, and 40 are provided so that a predetermined relationship exists between flexural stiffness exhibited by each of the zones. Flexural stiffness (FS) of each zone is defined by the following simplified formula:

$$FS = E \times t^3$$

where,

E=the elastic modulus or Young's modulus of the material of the zone; and t=the thickness of the zone.

The central zone 36 has a first flexural stiffness $FS_1$. The intermediate zone 38 has a second flexural stiffness $FS_2$. The perimeter zone 40 has a third flexural stiffness $FS_3$. The predetermined relationship between the portions is that the first flexural stiffness $FS_1$ is substantially greater than the second flexural stiffness $FS_2$, and optionally the third flexural stiffness $FS_3$ is substantially greater than the second flexural stiffness $FS_2$. Preferably, the first flexural stiffness $FS_1$ is at least three times greater than the second flexural stiffness $FS_2$. As a ratio the following relationship must be satisfied:

$$(FS_1/FS_2) \geq 3.$$

This expression means that the ratio of the central zone flexural stiffness $FS_1$ to the intermediate zone flexural stiffness $FS_2$ is equal to or greater than 3.0. When the above ratio of flexural stiffness is less than three, the central zone sustains excessive deformation during impact and accuracy of the club is diminished. More preferably, the first flexural stiffness $FS_1$ is at least six to twelve times greater than the second flexural stiffness $FS_2$. Most preferably, the first flexural stiffness $FS_1$ is about eight times greater than the second flexural stiffness $FS_2$.

Preferably, the third flexural stiffness $FS_3$ is at least two times greater than the second flexural stiffness $FS_2$. Thus, the following relationship must be satisfied:

$$(FS_3/FS_2) \geq 2.$$

In club head 10 (as shown in FIG. 3), the above flexural stiffness relationships are achieved by selecting a certain material with a particular elastic modulus and varying the thickness of the zones. In another embodiment, the flexural stiffness relationships can be achieved by varying the materials of the zones with respect to one another so that the zones have different elastic moduli and the thickness is changed accordingly. Thus, the thickness of the portions can be the same or different depending on the elastic modulus of the material of each portion. It is also possible to obtain the required flexural stiffness ratio through the use of structural ribs, reinforcing plates, and thickness parameters.

Quantitatively, it is preferred that the first flexural stiffness $FS_1$ is greater than 20,000 lb-in. When the first flexural stiffness is less than 20,000 lb-in excessive deformation of the central region can occur during impact and accuracy is diminished. More preferably, the first flexural stiffness $FS_1$ is greater than 55,000 lb-in. Preferably, the second flexural stiffness $FS_2$ is less than 16,000 lb-in. When the second flexural stiffness is greater than 16,000 lb-in the COR the resultant ball velocity is reduced. More preferably, the second flexural stiffness $FS_2$ is less than 10,000 lb-in and, most preferably, less than 7,000 lb-in.

Referring to FIG. 3, it is preferred that central portion 36 has a first area that is between about 15% and about 60% of the exterior surface area 32 or face area. The percentage of face area is computed by dividing the area of each zone 36, 38, or 40 by the total face area of exterior surface 32. It should be noted that the total face area of the exterior surface 32 is equivalent to the sum of areas of the zones 36, 38, and 40. In a preferred embodiment, the central zone first area is greater than about 15% and less than about 60% of the total face area. When the central zone 36 is less than 15% of the total face area, then accuracy can be diminished. When central portion 36 is greater than 60% of the face area 32, then COR can be diminished.

Referring again to FIG. 1, the club head 10 is further formed so that a center of gravity of the club head has a predetermined relationship with respect to a Cartesian coordinate system with a center located on the exterior surface and coincident with the geometric center GC of the face 16. The face includes a vertical centerline VCL and a horizontal centerline HCL perpendicular thereto. The geometric face center GC is at the intersection of these centerlines VCL and HCL. Preferably, the geometric center of the central zone 36 is coincident with the club face geometric center GC.

Figure 1:
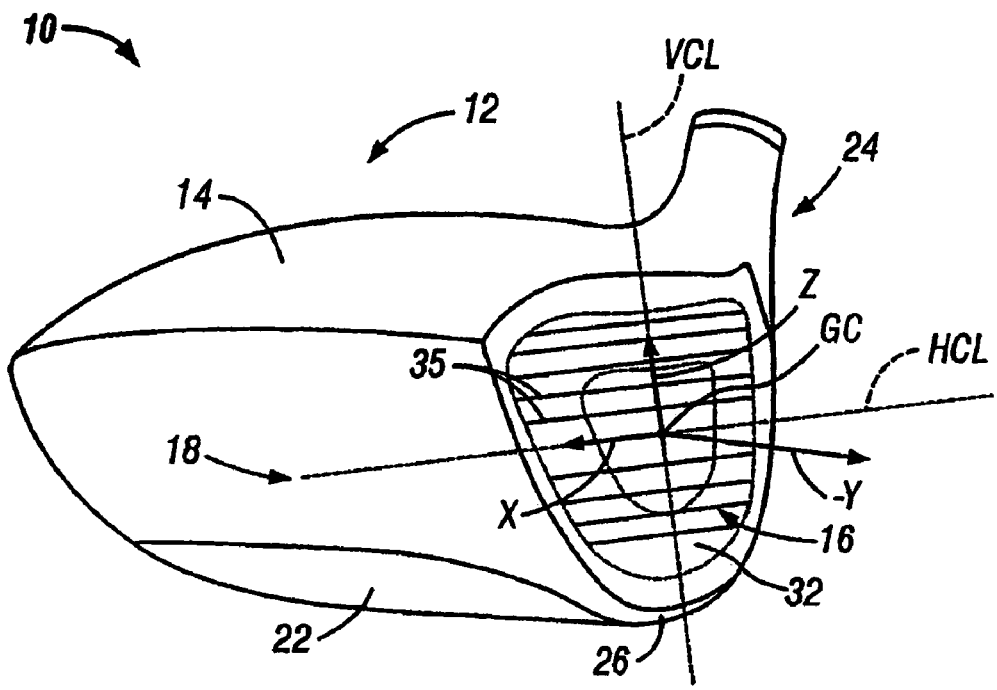
FIG. 1 is a toe side, front, and perspective view of a first embodiment of a golf club head of the present invention.
Figure 2:
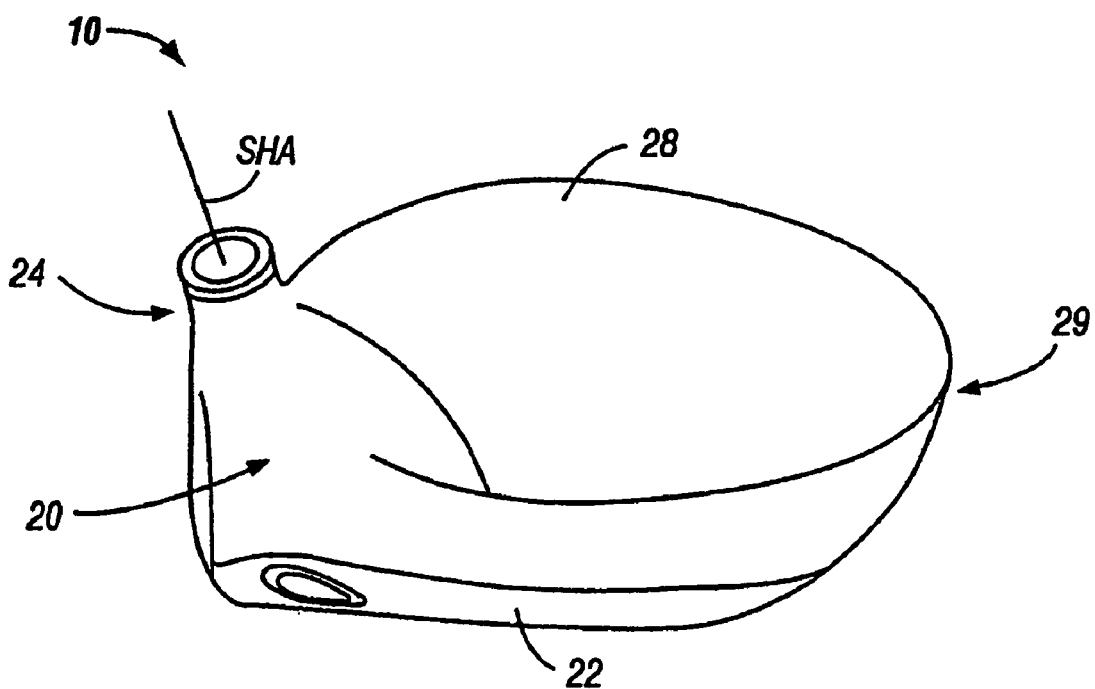
FIG. 2 is a heel side, rear, and perspective view of the golf club head of FIG. 1.

The Cartesian coordinate system is defined when the club head is resting on a flat surface (i.e., at its natural loft) and includes three axes, as illustrated in FIG. 1. The origin of the Cartesian coordinate system preferably coincides with the geometric center of the hitting face. The X-axis is a horizontal axis positioned tangent to the geometric center of the hitting face with the positive direction toward the heel of the club. The Y-axis is another horizontal axis orthogonal to the X-axis with the positive direction toward the rear of the club. The Z-axis is a vertical axis orthogonal to both the X-axis and Y-axis with the positive direction toward the crown of the club. The center of gravity is preferably located behind and lower than the geometric center of the face.

Referring to FIG. 1, the location of the center of gravity is defined by coordinates for the center of gravity $CG_z$, $CG_y$, and $CG_x$ with respect to the Z, X, and Y axes, respectively. In the vertical direction along the Z-axis, the center of gravity coordinate is designated $CG_z$, and is spaced a first distance D1 from the geometric face center G along the Z-axis. The first distance D1 is at least about −0.1 inches, and more preferably the first distance D1 is at least about −0.15 inches so that the center of gravity in the vertical direction is below the geometric center GC.

In the horizontal direction along the X-axis, the center of gravity coordinate is designated $CG_x$, and is spaced a second distance D2 from the geometric face center GC. The second distance D2 is less than about 0.02 inches and greater than −0.02 inches so that the center of gravity in the horizontal direction is spaced from the center GG by no further than the magnitude of distance D2.

Referring to FIG. 1, along the Y-axis, the center of gravity coordinate is designated $CG_y$, and is spaced a third distance D3 from the geometric face center GC preferably toward the rear portion 29. The center of gravity $CG_y$ in the third direction is spaced from the center GC toward the rear portion 29 by no further than the magnitude of the third distance D3. The third distance D3 is preferably equal to or less than about 1.25 inches and, more preferably, less than about 1 inch.

EXAMPLES

These and other aspects of the present invention may be more fully understood with reference to the following non-limiting examples, which are merely illustrative of embodiments of the present invention golf club head, and are not to be construed as limiting the invention, the scope of which is defined by the appended claims.

TABLE 1

FLEXURAL STIFFNESS INFORMATION

| Parameter | Comparative Example 1 | Comparative Example 2 | Comparative Example 3 | Inventive Example |
|---|---|---|---|---|
| Thickness of Center Zone (inches) | 0.115 | 0.130 | 0.095 | 0.150 |
| Thickness of First Intermediate Zone (inches) | 0.115 | 0.100 | 0.098 | 0.075 |
| Thickness of Second Intermediate Zone (inches) | 0.115 | 0.080 | 0.100 | 0.075 |
| Thickness of Perimeter Portion (inches) | 0.115 | 0.150 | 0.120 | 0.120 |
| E of All Portions (psi) | 1.65E+07 | 1.65E+07 | 1.65E+07 | 1.65E+07 |
| FS of Center Portion (lb-in) | 25094 | 36251 | 14147 | 55688 |
| FS of First Intermediate zone (lb-in) | 25094 | 16500 | 15530 | 6961 |
| FS of Second Intermediate Zone (lb-in) | 25094 | 8448 | 16500 | 6961 |
| FS of Perimeter Zone (lb-in) | 25094 | 55688 | 28512 | 28512 |
| $FS_1/FS_2$ | 1.0 | 2.2 | 0.9 | 8.0 |
| $FS_3/FS_2$ | 1.0 | 3.4 | 1.8 | 4.1 |

Comparative Examples 1–3 are club heads configured and dimensioned as indicated above with materials so that the zones have certain values. As a result, the ratio of the central zone flexural stiffness and adjacent intermediate zone flexural stiffness for the Comparative Examples are 1.0, 2.2, and 0.9. These ratios are outside of the preferred ratio that ($FS_1/FS_3 \geq 3$) in accordance to one aspect of the present invention. On the other hand, the Inventive Example is configured and dimensioned so that ($FS_1/FS_3$=about 8). In the examples above, the intermediate zone is defined by a first intermediate zone adjacent the central zone and a second intermediate zone adjacent the first intermediate zone. The perimeter zone is adjacent the intermediate zone(s).

Comparative Examples 1 and 3 have a ratio of $FS_3/FS_2$ of 1.0 and 1.8, respectively. These ratios are also outside of the preferred ratio ($FS_3/FS_2 \geq 2$) in accordance to another aspect of the present invention. Comparative Example 2 and the Inventive Example satisfy such a ratio with values of about 3.4 and 4.1, respectively.

TABLE 2

CENTER OF GRAVITY INFORMATION

| Parameter | Comparative Example 1 | Comparative Example 2 | Comparative Example 3 | Inventive Example |
|---|---|---|---|---|
| $CG_z$ Location (inches)[1] | 0.074 | 0.074 | 0.074 | −0.120 |
| $CG_x$ Location (inches)[2] | 0.133 | 0.137 | 0.137 | −0.001 |
| $CG_y$ Location (inches)[3] | 1.159 | 1.159 | 1.182 | 0.991 |

[1]Positive z is toward the crown from GC
[2]Positive x is toward the toe from GC
[3]Positive y is toward the back from the GC The center of gravity for the Inventive Example club head was achieved by the configuration and dimensions of the club head in additional to adding a weight of 31.5 grams to the sole plate. Other known methods of weight manipulation can be used to achieve the inventive center of gravity location as set forth above.

Thus, referring to FIG. 1, in the club head example of the present invention the center of gravity is preferably located along the Z-axis at least 0.10 inches below the geometric face center GC, along the X-axis within 0.01 inches from the geometric face center GC, and along the y-axis within 1.25 inches from the geometric face center GC. The Parameter column of Table 2 describes for each center of gravity location or coordinate the distance that the center of gravity is spaced from the face geometric center GC with respect to a Cartesian coordinate system along particular axes. The centers of gravity for Comparative Examples 1–3 are not located properly with respect to the inventive requirements along the Z- and X-axes. The center of gravity for the Inventive Example is located properly with respect to the inventive requirements in the Z, X, and Y axes.

TABLE 3

TEST RESULTS

| Parameter | Comparative Example 1 | Comparative Example 2 | Comparative Example 3 | Inventive Example |
|---|---|---|---|---|
| Maximum COR | 0.807 | 0.808 | 0.829 | 0.830 |
| Average COR | 0.765 | 0.766 | 0.783 | 0.789 |
| Maximum Total Distance (yards) | 290 | 286 | 291 | 298 |
| Landing Area (yards²) | 950 | 255 | 1000 | 341 |

The test results enumerated in Table 3 were generated using computational techniques, which included finite element analysis models. When computer modeling the exemplary club heads, the following assumptions were made: club head loft of 8.5°; club head mass of 201 grams; and club head material is 6AL-4V titanium alloy. The golf ball used was a two-piece solid ball. Finite element models were used to predict ball launch conditions and a trajectory model was used to predict distance and landing area. The impact condition for the swing used in the total distance and landing area predictions or tests had a club head velocity of 109.1 mph and an attack angle of +2 degrees, the club was oriented such that the vertical plane of the face was at an angle of 8.5 degrees relative to the velocity vector. The impact condition used for club coefficient of restitution (COR) tests was consistent with the USGA Rules for Golf, specifically, Rule 4-1e Appendix II Revision 2 dated Feb. 8, 1999.

COR or coefficient of restitution is one way of measuring ball resiliency. The coefficient of restitution (COR) is the ratio of the velocity of separation to the velocity of approach. In this model, therefore, COR was determined using the following formula:

$$(v_{club\text{-}post} - v_{ball\text{-}post})/(v_{ball\text{-}pre} - v_{club\text{-}pre})$$

where, $v_{club\text{-}post}$ represents the velocity of the club after impact;
$v_{ball\text{-}post}$ represents the velocity of the ball after impact;
$v_{club\text{-}pre}$ represents the velocity of the club before impact (a value of zero for USGA COR conditions); and
$v_{ball\text{-}post}$ represents the velocity of the ball before impact.

COR, in general, depends on the shape and material properties of the colliding bodies. A perfectly elastic impact has a COR of one (1.0), indicating that no energy is lost, while a perfectly inelastic or perfectly plastic impact has a COR of zero (0.0), indicating that the colliding bodies did not separate after impact resulting in a maximum loss of energy. Consequently, high COR values are indicative of greater ball velocity and travel and total distance. Club heads with thinner faces also have higher COR values, as exhibited by Comparative Example 3 as compared to the Comparative Club 1. However, unexpectedly the Inventive Example has the highest COR. For the inventive club head, preferably the COR is greater than about 0.81, and more preferably greater than about 0.83.

It is expected that as COR increases the ball flight distance will increase and the maximum total distance will also increase. The Inventive Example has the highest COR and also the highest maximum total distance.

It as also expected that as COR increases the shot accuracy will decrease. However, the Inventive Example has the highest COR and the greatest accuracy as illustrated by the data for Landing Area. The Landing Area is an area encompassing the position of nine balls, which impact the club face at various locations. The nine impact locations were equally spaced within a rectangular region 1 inch wide and 0.5 inches high, centered on the geometric center of the club face. The club head of the Inventive Example has a very small Landing Area of 341 square yards. The Comparative Example 3, which is the only Comparative Example with a sufficient COR of at least 0.81, has a Landing Area of 1000 square yards, which is significantly greater than the Landing Area for the Inventive Club. The smaller the landing area, the greater the accuracy of the club.

Several alternative embodiments of the invention are possible. The features of the invention include flexural stiffness for distinct zones or portions of the club face, as well as the ratio of flexural stiffness between portions. A wide variety of rib configurations and material alternatives may be used to attain the requisite flexural stiffness and flexural stiffness ratio of the face portions.

In FIGS. 3–3B, a preferred embodiment of the club 10 is shown. The club 10 has a face 16 with the following construction. The central zone 36 has a thickness, $t_1$, of about 0.150 inches, the intermediate zone 38 has thickness, $t_2$, of about 0.075 inches, and the perimeter zone 40 has thickness, $t_3$, of about 0.120 inches. Furthermore, the central zone 36 comprises about 20% of the total face surface area and the perimeter zone 40 is less than about 20% of the total face surface area. Each of the three zones 36, 38, and 40 has uniform thickness within the zone and are constructed from a single homogeneous material, preferably a titanium alloy, with a Young's modulus (E) of approximately $16.5 \times 10^6$ lbs/in$^2$.

Referring to FIGS. 3–3B, the flexural stiffness, $FS_z$, can also be defined by the following general equation:

$$FS_z = \sum_{i=1}^{n} \frac{A_i}{\sum_{j=1}^{n} A_j} E_i t_i^3$$

where;
$A_i$ is defined as the area of a constituent within a zone,
$E_i$ is the Young's modulus in pounds per square inch of the constituent within a zone, $$\sum_{j=1}^{n} A_j$$

represents the total area of the zone,
$t_i$ is the thickness or average thickness in inches of a constituent within a zone,
n is the number of constituents within a zone.

This general equation reduces to the simplified equation $FS_z = Et^3$, stated above when each zone has a uniform thickness and a constant Young's modulus.

Using this simplified equation, the flexural stiffness can be calculated for the central and abutting zones and the flexural stiffness ratio can be computed. The flexural stiffness ratio for the preferred embodiment golf club head 10 is calculated as, $$FS_c = E_c t_c^3$$
$$= (16.5 \times 10^6 \text{ lb/in}^2)(0.15 \text{ in})^3$$
$$= 55,689 \text{ lb·in, and}$$

$$FS_I = E_I t_I^3$$
$$= (16.5 \times 10^6 \text{ lb/in}^2)(0.075 \text{ in})^3$$
$$= 6,961 \text{ lb·in,}$$

where $FS_C$ is the flexural stiffness of central region 36 (also denoted $FS_1$ as herein) and $FS_I$ is the flexural stiffness of intermediate region 38 (also denoted $FS_2$ as herein). These values are also reported in Table 1, above. Hence, the ratio of flexural modulus of golf club head 10 is $(FS_C/FS_I) = 8.0.$ In FIG. 6, an alternate embodiment of the club head 110 is shown to illustrate an alternate construction of hitting face 116 that results in a similar flexural stiffness ratio of the central portion to the abutting intermediate zone as the embodiment of FIG. 3. In the club head 110, the face 116 has an elliptically shaped central zone 136 an adjacent intermediate zone 138. The central zone 136 occupies about 30 percent of the total face surface area.

Referring to FIGS. 7–7B, the central zone 136 includes a ribbed support structure 137a (shown in phantom) that extends from the interior surface of the face. The asterisk-shaped ribbed structure, which comprises a plurality of ribs or legs, stiffens the central zone. The thickness of the ribbed portion 137a of the central zone $t_{1A}$ is about 0.225 inches. The width of the rib, w, is about 0.085 inches. The thickness of the remaining portion 137b between the ribs of the central zone $t_{1B}$ is about 0.09 inches. The ribbed structure 137a is defined such that it comprises about 25 percent of the surface area of the central zone. The intermediate zone 138 has a uniform thickness, $t_2$, of about 0.075 inches and extends to the boundary of the face 116 with no defined perimeter zone. The face 116 is preferably made of a homogeneous titanium alloy with a Young's modulus (E) of $16.5 \times 10^6$ lbs/in$^2$.

Referring to FIGS. 6–7B, the flexural stiffness ratio between the central region 136 and the abutting intermediate zone 138 is computed, as follows:

Area of the elliptical central region 136 is $A_C = \pi \times b \times a$, where "b" is ½ of the major axis of the ellipse and "a" is ½ of the minor axis of the ellipse. When the major axis is 2 inches and the minor axis is 1 inch, the area of the central region is 1.57 in$^2$.

The area of the ribs is simply its width (WI=0.085 inch) times its length (LI=4.6 inch) or $A_r = WI \times LI = 0.39$ in$^2$.

Hence, the non-rib area $A_{NR} = A_c - A_r = (1.57 - 0.39) = 1.18$ in$^2$.

Thus, the general flexural stiffness equation stated above reduces to $$FS_c = (A_r/A_C)E(t_{1A})^3 + (A_{NR}/A_C)E(t_{2B})^3,$$

$$FS_c = (0.39/1.57)(16.5 \times 10^6 \text{ lb/in}^2)(0.225 \text{ in})^3 + (1.18/1.57)(16.5 \times 10^6 \text{ lb/in}^2)(0.090 \text{ in})^3,$$

$$FS_c = 56,008 \text{ lb·in, and}$$

$$FS_I = E(t_2)^3,$$
$$= (16.5 \times 10^6 \text{ lb/in}^2)(0.075 \text{ in})^3,$$
$$= 6,961 \text{ lb·in.}$$

Hence, $(FS_c/FS_I) = 8.05.$

It should be noted that ribs, welts, pimples, or other discrete thickness variations within a zone are handled as discrete elements within a particular zone and are computed in accordance with the governing general equation for flexural stiffness discussed above.

Figure 8:
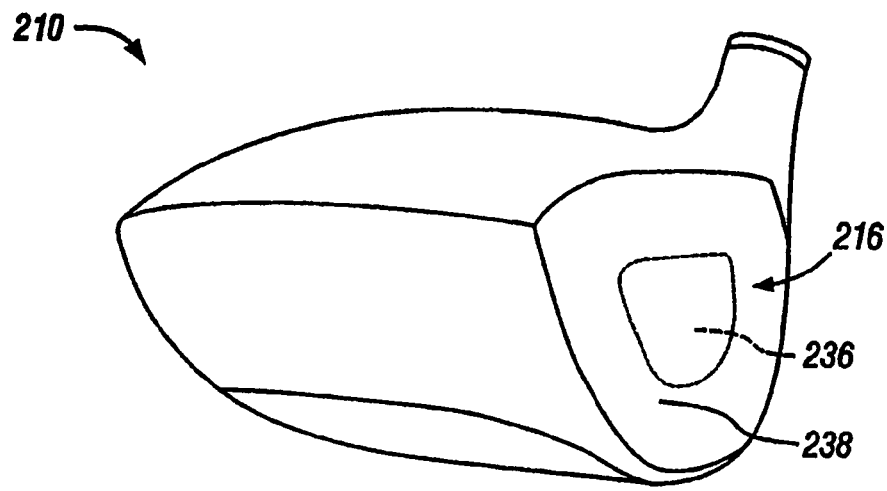
FIG. 8 is a toe side, front, and perspective view of a third embodiment of a golf club head of the present invention.

In FIG. 8, an alternate embodiment of the club head 210 is shown to illustrate an alternate construction of face 216 that results in a similar flexural stiffness ratio of the central zone to the abutting intermediate zone as the embodiment of FIG. 3. In the club head 210, the face 216 has a central zone 236 and an adjacent intermediate zone 238. The central zone 236 is about 30 percent of the total face surface area. The club head 210 does not have a defined perimeter zone.

Figure 9:
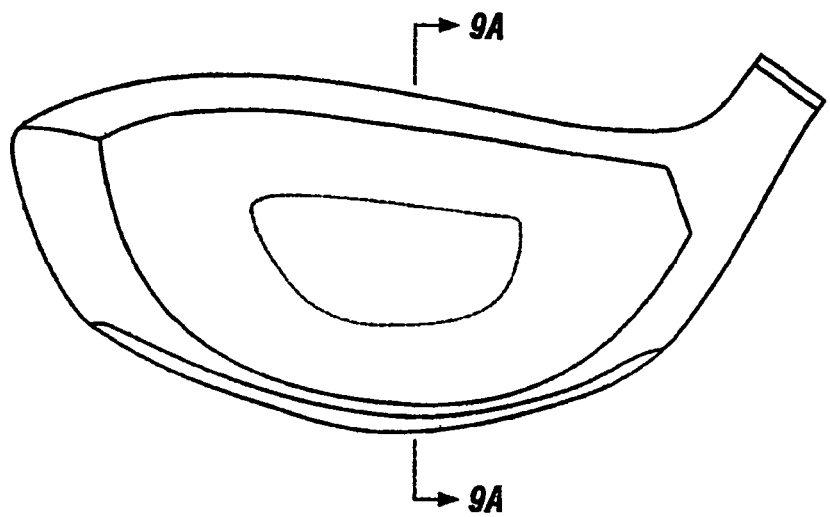
FIG. 9 is a front, elevational view of the golf club head of FIG. 8.
Figure 9A:
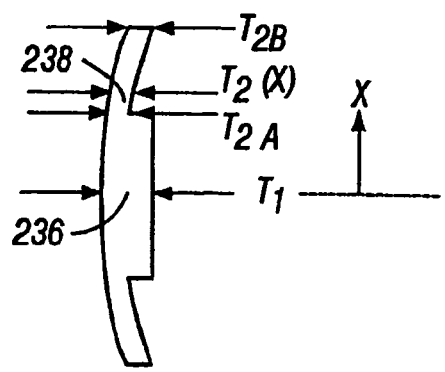
FIG. 9A is a cross-sectional view of the face of the golf club head of FIG. 9 along line 9A—9A.

Referring to FIGS. 9–9A, the central zone 236 has a uniform thickness of $t_1$ of about 0.140 inches. The intermediate zone 238 has a continuously tapered thickness from the face perimeter inward to the central zone 236. The thickness of the intermediate zone 238 is defined to change linearly.

The intermediate zone 238 has an inner thickness, $t_{2A}$, of about 0.07 inches at the boundary of the central zone 236 and the intermediate zone 238. The intermediate zone 238 has an outer thickness, $t_{2B}$, of about 0.10 inches. The outer thickness is at the face perimeter. In instances of non-uniform thickness, within a zone, and primarily in relation to a continuous tapered zone, an average thickness may be used to compute the flexural stiffness for the zone. This approximation simplifies the calculation and is physically based on elastic shell theory.

In this embodiment, two different homogenous materials are used. The central zone 236 is preferably made from a stainless steel having a Young's modulus of $30.0 \times 10^6$ lbs/in$^2$ and the adjacent intermediate zone 238 is made from a titanium alloy with a Young's modulus of $16.5 \times 10^6$ lbs/in$^2$.

Referring to FIGS. 8–9A, the flexural stiffness ratio between the central and adjacent zone is computed.

$$FS_c = E_c(t_1)^3,$$
$$= (30 \times 10^6 \text{ lb/in}^2)(0.140 \text{ in})^3,$$
$$= 82,320 \text{ lb} \cdot \text{in},$$
$$FS_I = E_I((t_{2A} + t_{2B})/2)^3,$$
$$= (16.5 \times 10^6 \text{ lb/in}^2)((0.1 + 0.07)\text{in}/2)^3,$$
$$= 10,133 \text{ lb} \cdot \text{in}.$$

Hence, $(FS_c/FS_I) = 8.12$.

Figure 10:
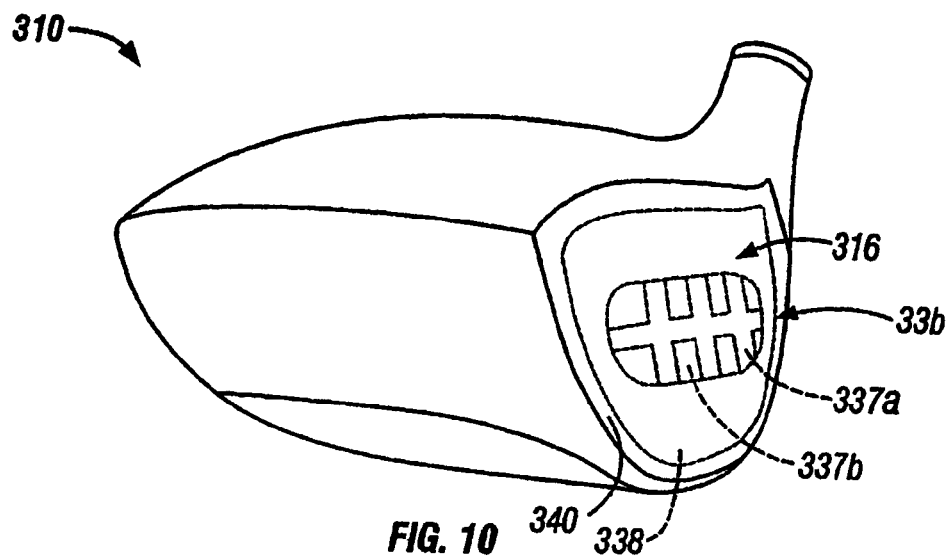
FIG. 10 is a toe side, front, and perspective view of a fourth embodiment of a golf club head of the present invention.

In FIG. 10, an alternate embodiment of the club head 310 is shown to illustrate an alternate construction of face 316 that results in a similar flexural stiffness ratio of the central zone to the abutting intermediate zone as the embodiment of FIG. 3. In the club head 310, the face 316 has an elliptically shaped central zone 336 and an adjacent intermediate zone 338. The central zone 336 is formed using two materials 337a (shown in phantom) and 337b (shown in phantom).

The central zone 336 has a uniform thickness, $t_1$, of about 0.140 inches. The first material 337a is a titanium alloy with a Young's modulus of $16.5 \times 10^6$ lbs/in$^2$. The second material 337b is stainless steel and has a Young's modulus of $30 \times 10^6$ lbs/in$^2$. The central zone 336 comprises about 60 percent stainless steel.

Furthermore, the central zone 336 is elliptically shaped and comprises about 25 percent of the total face surface area. The intermediate zone 338 with the perimeter zone 340 comprises of no more than 20 percent of the total face surface area. The intermediate zone has a uniform thickness, $t_2$, of about 0.08 inches and is constructed from the same titanium alloy as the central zone 336.

Figure 11:
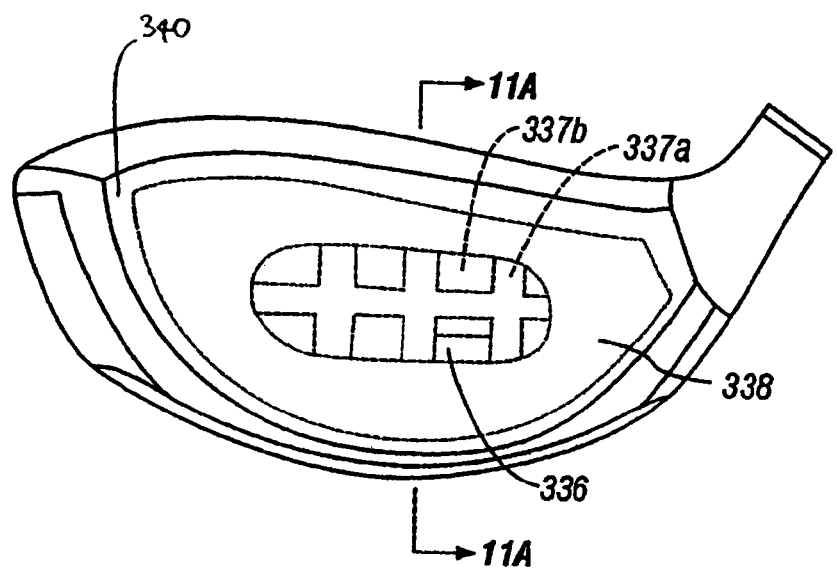
FIG. 11 is a front, elevational view of the golf club head of FIG. 10.
Figure 11A:
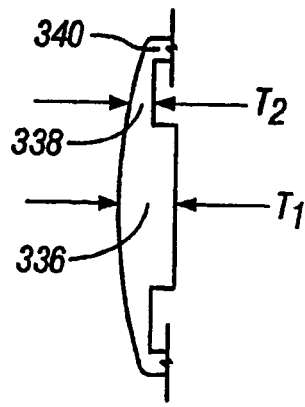
FIG. 11A is a cross-sectional view of the face of the golf club head of FIG. 11 along line 11A—11A.

Referring to FIGS. 10–11A, the flexural stiffness ratio between the central region 336 and intermediate zone 338 can be computed, as follows.

Using the equation for determining the area for an ellipse, stated above, when the major axis is about 1.8 inch and the minor axis is about 0.9 inch, the area of central region 336 is $A_C = 1.272$ in$^2$. As discussed above, the area of stainless steel ($A_S$) is 60 percent and the area of titanium or non-steel ($A_{NS}$) is 40 percent.

$$FS_c = (A_S/A_C)E_s(t_1)^3 + (A_{NS}/A_C)E_t(t_1)^3,$$

$$FS_c = (0.60)(30 \times 10^6 \text{ lb/in}^2)(0.14 \text{ in})^3 + (0.40)(16.5 \times 10^6 \text{ lb/in}^2)(0.14 \text{ in})^3,$$

$$FS_c = 67,502 \text{ lb} \cdot \text{in, and}$$

$$FS_I = E_t(t_2)^3,$$
$$= (16.5 \times 10^6 \text{ lb/in}^2)(0.080 \text{ in})^3,$$
$$= 8,448 \text{ lb} \cdot \text{in}.$$

Hence, $(FS_c/FS_I) = 8.0$.

The golf club head embodiments 10, 110, 210, and 310 discussed in FIGS. 1–11A demonstrate four unique face constructions which result in a similar flexural stiffness ratio, where the central zone to the adjacent zone ratio is greater than or equal to three and, more particularly, about eight. In cases where the face construction is uncertain due to manufacturing tolerances or methods or for other possible reasons, a nondestructive test method of determining the flexural stiffness ratio for a given face construction may be used.

Figure 12:
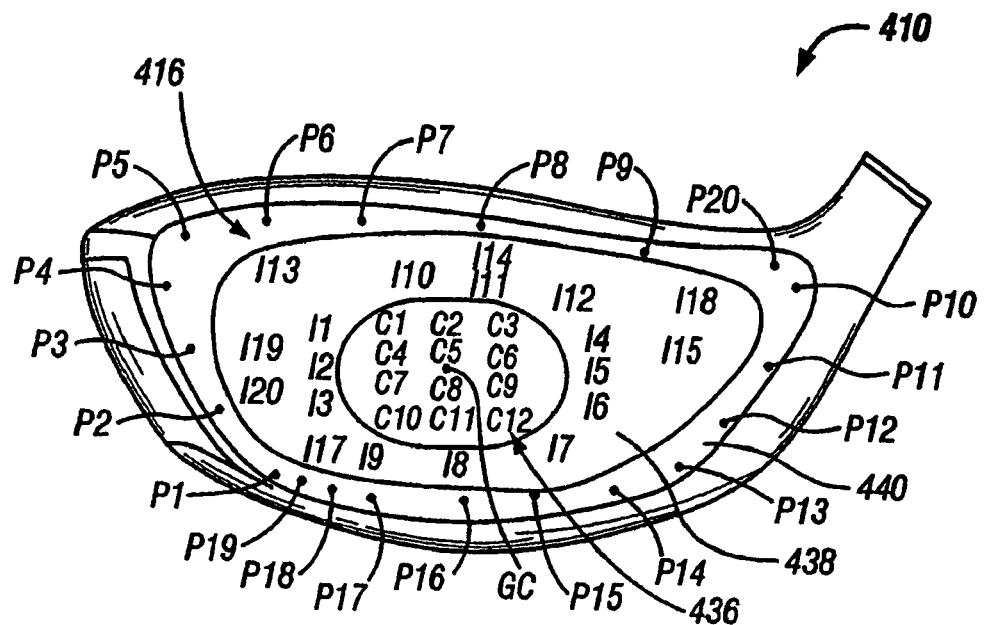
FIG. 12 is an enlarged, front view of a golf club head with ultrasonic thickness measurement locations indicated.

Referring to FIG. 12, a typical club 410 is shown with an unknown face thickness profile. Preferably, something is known regarding the construction materials of the face or has been determined experimentally through test methods known to those of ordinary skill in the art. In FIG. 12, a random distribution of points is shown on face 416. This distribution is referred to herein as a "point cloud" or predetermined point distribution. Points labeled C indicate a position in the central zone 436. Points labeled I indicate a position in the intermediate zone 438. Points labeled P indicate a position in the perimeter zone 440. The numbers following the position letters "C", "I" or "P" indicate relative face position.

Figure 13:
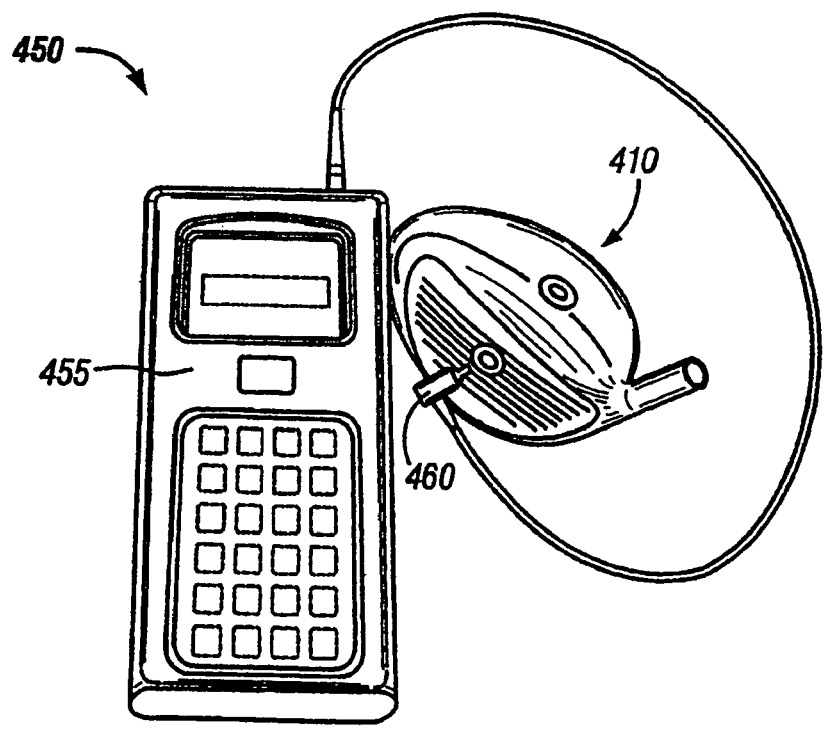
FIG. 13 is a schematic representation of the apparatus for taking an ultrasonic thickness measurement on the face of a club head.

Using the defined point cloud, an ultrasonic measurement device 450 (as shown in FIG. 13) can be used to map the face 416 thickness profile. The point cloud technique has the advantage of capturing discrete variations in face thickness such as the presence of ribs or abrupt thickness changes. One preferred ultrasonic measurement device includes a Panametrics Model 25DL ultrasonic thickness device 455 and a Panametrics model M208 probe 460. The sensor or device 455 and the probe or transducer 460 are commercially available from Panametrics, Inc. of Waltham, Mass.

Referring to FIG. 12, the face thickness data obtained from the ultrasonic measurement, along with material modulus information, is then used to define the central, intermediate and possibly perimeter zones. The central zone 436 is defined by constructing an area comprising of a specific percentage of the total face surface area and including the geometric center GC. The point cloud thickness data within the defined zone is then averaged or broken into distinct elements within the zone. If the latter is required, the area percentages for the elements within the zone are calculated. The calculation for FSz previously outlined is then carried out to determine the flexural stiffness ratio between the central and adjacent zone 436 and 438, respectively.

The following example illustrates the technique. In Table 4, random face thickness measurements are shown for titanium alloy club 410 (as shown in FIG. 12) with an unknown face thickness profile. The technique described above is used.

TABLE 4

ULTRASONIC FACE THICKNESS DATA

| Position | Thickness |
| --- | --- |
| C1 | 0.132 |
| C2 | 0.127 |
| C3 | 0.131 |
| C4 | 0.125 |
| C5 | 0.136 |
| C6 | 0.130 |
| C7 | 0.127 |
| C8 | 0.129 |
| C9 | 0.133 |
| C10 | 0.138 |
| C11 | 0.134 |
| C12 | 0.131 |
| I1 | 0.102 |
| I2 | 0.103 |
| I3 | 0.098 |
| I4 | 0.096 |
| I5 | 0.088 |
| I6 | 0.089 |
| I7 | 0.089 |
| I8 | 0.094 |
| I9 | 0.097 |
| I10 | 0.099 |
| I11 | 0.100 |
| I12 | 0.103 |
| I13 | 0.106 |
| I14 | 0.102 |
| I15 | 0.105 |
| I16 | 0.101 |
| I17 | 0.100 |
| I18 | 0.103 |
| I19 | 0.107 |
| I20 | 0.106 |
| P1 | 0.110 |
| P2 | 0.115 |
| P3 | 0.117 |
| P4 | 0.119 |
| P5 | 0.120 |
| P6 | 0.114 |
| P7 | 0.117 |
| P8 | 0.109 |
| P9 | 0.108 |
| P10 | 0.111 |
| P11 | 0.115 |
| P12 | 0.118 |
| P13 | 0.109 |
| P14 | 0.108 |
| P15 | 0.112 |
| P16 | 0.112 |
| P17 | 0.115 |
| P18 | 0.109 |
| P19 | 0.117 |
| P20 | 0.120 |

FIG. 12 shows the measured data points and the projected central, intermediate and perimeter zones 436, 438, and 440. Based on these projected areas, the percentage of each zone can be estimated or computed more accurately by other techniques, such as face scanning. The data defines three zones, the actual central zone with an average thickness of 0.131 inches; the actual intermediate zone with an average thickness of 0.099 inches, and the perimeter zone with an average thickness of 0.114 inches. Furthermore, the area of the central zone has been estimated to be about 23 percent of the total face surface area, and the perimeter zone is estimated to comprise of about 35 percent of the total face area. Based on this information a flexural stiffness ratio can be computed as set forth below.

With regard to the calculation of face flexural stiffness and the flexural stiffness ratio, the aforementioned embodiments and point cloud example all consider hitting faces, which possess isotropic material property and symmetry with regard to a mid-surface of the face structure. Material isotropy, however, in not a necessary condition of the invention. And the invention can include club heads with anisotropic materials. The flexural stiffness or the flexural stiffness ratio can be used with anisotropic constructions. These calculations would still be applicable but of a more general form, as discussed below.

The notion of symmetry with regard to a mid-surface of the face simplifies the calculations of flexural stiffness. The calculation of flexural stiffness for asymmetric shell structures with respect to the mid-surface is common in composite structures where laminate shell theory is applicable. Here the Kirkhoff shell assumptions are applicable. Referring to FIG. 14, an asymmetric isotropic laminate 500 is shown with N lamina or layers 502. Furthermore, the laminate is described to be of thickness, t, with $x_i$ being directed distances or coordinates in accordance with FIG. 14. The positive direction is defined to be downward and the laminate points $x_i$ defining the directed distance to the bottom of the $k^{th}$ laminate layer. For example, $x_0=-t/2$ and $x_N=+t/2$ for a laminate of thickness t made comprised of N layers.

Further complexity is added if the lamina can be constructed of multiple materials, M. In this case, the area percentage, Ai is included in the flexural stiffness calculation, as before in a separate summation over the lamina. The most general form of computing the flexural stiffness in this situation is, as stated above:

$$FS_z = \sum_{i=1}^{n} \frac{A_i}{\sum_{j=1}^{n} A_j} E_i t_i^3$$

Due to the geometric construction of the lamina about the mid-surface, asymmetry results, i.e., the laminate lacks material symmetry about the mid-surface of the laminate. However, this asymmetry does not change the calculated values for the flexural stiffness only the resulting forces and moments in the laminate structure under applied loads. An example of this type of construction would be a titanium alloy face of uniform thickness and first modulus $E_t$, where the central zone is backed by a steel member of width half the thickness of the titanium portion, and having second modulus $E_s$. In this example, the flexural stiffness can be approximated by the simplified equation, as follows:

$$FS_z = \frac{1}{3} \sum_{i=1}^{M} [E(x_k^3 - x_{k-1}^3)]_i$$

$$FS_z = \frac{1}{3} \{[E_s(x_o^3 - x_1^3)] + E_t(x_1^3 - x_2^3)]\}$$

here, $x_o=-t/2$, $x_1=t/2-WI$ and $x_2=t/2$, substitution yielding $$FS_z = \frac{1}{3} \{[E_s((-t/2)^3 - (t/2-WT)^3)] + E_t((t/2)^3)]\}$$

If t=0.125, then WI=0.083 and FS of this zone is 3,745 lb·in, where the thickness of the steel layer is about one-half of the thickness of the titanium layer.

Referring to FIG. 15, a testing apparatus 650 for measuring inertance is schematically illustrated. Generally, inertance is a frequency response. More specifically, inertance is a measure of the stiffness of a structure, in this instance the club face, at various frequencies of vibration. The units of inertance are acceleration units over force units. A preferred first resonant frequency for the inventive face is located where the inertance is maximized.

The test apparatus 650 includes club head 652, a rigid mass 654, an accelerometer 656, and an impact hammer 658. The mass 654 is preferably a cylindrical steel rod with a diameter of 1 inch. Referring to FIGS. 15 and 15A, the mass 654 preferably has a cylindrical cavity 659 at one end for receiving the accelerometer 656 and a slot 660 to accommodate the cable 662. The accelerometer 656 is connected to the geometric center of the face of the club head 652 with a high modulus adhesive 657, such as a cyanoacrylate based adhesive, Loctite 409, available from Loctite Corp., Newington, Conn. The mass 654 is then placed over the accelerometer 656 and also secured to the club face with cyanoacrylate adhesive. The combined mass of the mass 654 and the accelerometer 656 should equal the mass of a golf ball or 1.62 oz. The impact hammer 658 has an integral force transducer 658a and is movable toward and away from the free end 654a of the rigid mass, as indicated by the arrow I, to impact the mass 654, which is attached to the club head face at the geometric center. The impact force or excitation force is normal to the club face, and upon impact is transmitted to the hitting face through the mass 654.

The testing apparatus 650 further includes a junction box and ICP power supply 660 and cables 662 electrically connected to the accelerometer 656 and the impact hammer transducer 658a. The junction box and ICP power supply 660 is in turn connected to a digital signal processing board 664, located within a computer 665 with signal processing software 667. The digital signal processing board 664, computer 665 and software 667 are used to condition frequency signals and calculate the frequency response functions. The accelerometer 656, transducer 658a, junction box and ICP power supply 660, cables 662, digital signal processing board 664, computer 665, and software 667 are commercially available and one of ordinary skill in the art can readily identify and obtain inertance values for golf clubs using these components. Typically, the data from 20 impacts are averaged to reduce noise and improve measurement accuracy. The following TABLE 5 lists specific model numbers for the vibration equipment shown in FIG. 13.

TABLE 5

VIBRATION EQUIPMENT

| Reference Number | Part | Model # | Supplier |
|---|---|---|---|
| 656 | Accelerometer | 352A10 | Modal Shop of Cincinnati, OH |
| 658 | Impact Hammer | 086C01 | Modal Shop |
| 662 | Cables | 002T01 | Modal Shop |
| 660 | Junction Box & ICP power | BNC 2140 | National Instruments of Dallas, TX |
| 664 | DSP Board | NI 4551 | National Instruments |
| 665 | Computer | Dell Optiplex Gxi | Dell Computers of Round Rock, TX |
| 667 | Software | Virtual Bench DSA 2.5.1 | National Instruments |

Figure 16:
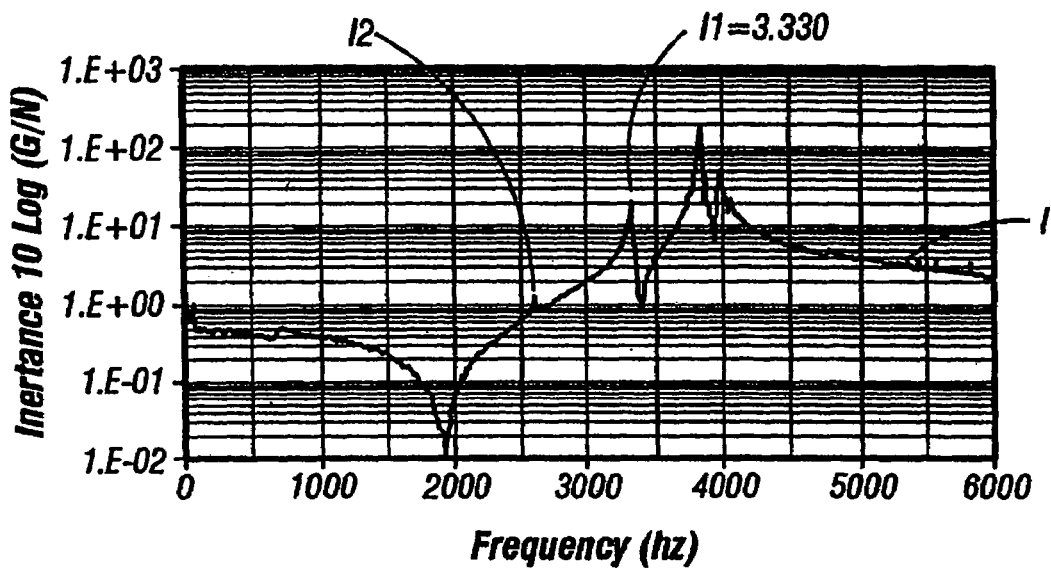
FIG. 16 is a graph of inertance versus frequency for a conventional club head.

Referring to FIG. 16, a graph of inertance versus frequency for a conventional club head is shown. The conventional club head is a Callaway Great Big Bertha War Bird with an eight degree loft. The inertance I shown is the result of testing using apparatus 650 of FIG. 15. The point $I_1$ at a frequency of 3330 Hertz represents the first primary resonant frequency, which occurs at the first primary maxima inertance for the inertance function I. A maxima, which does not represent a primary resonant natural frequency of the face, is also present in FIG. 16 at a frequency of 2572 Hertz, which is the point $I_2$. These secondary maxima $I_2$ are characterized by inertance transitions of a magnitude of less than 10 decibels. These secondary maxima may be due to crown, sole or skirt vibrations that are not acting perpendicular to the plane of the club face. Secondary maxima do not correlate with COR and ball velocity, since the vibration response is either small in magnitude or alternately not coincident with ball response. The COR for the conventional club head tested was measured in accordance with USGA, Rule 4-1e Appendix II Revision 2 dated Feb. 8, 1999 and was found to be 0.785. The preferred first primary resonant frequency of vibration is defined by the following relationship:

$$1/(2 \times \text{contact duration}) < I_1 < 3/(2 \times \text{contact duration})$$

The contact duration is the time interval during which the ball is in contact with the club face. The contact duration for a typical driver impact is about 500 microseconds ($500 \times 10^{-6}$ second). Thus, the preferred primary resonant frequency of vibration for the club head is between about 1000 and 3000 Hz. The closer the contact time is to the lower limit, the higher the COR and thus the higher the rebound ball velocity. More preferably, the first primary resonant frequency is less than 2900 Hz.

Figure 17:
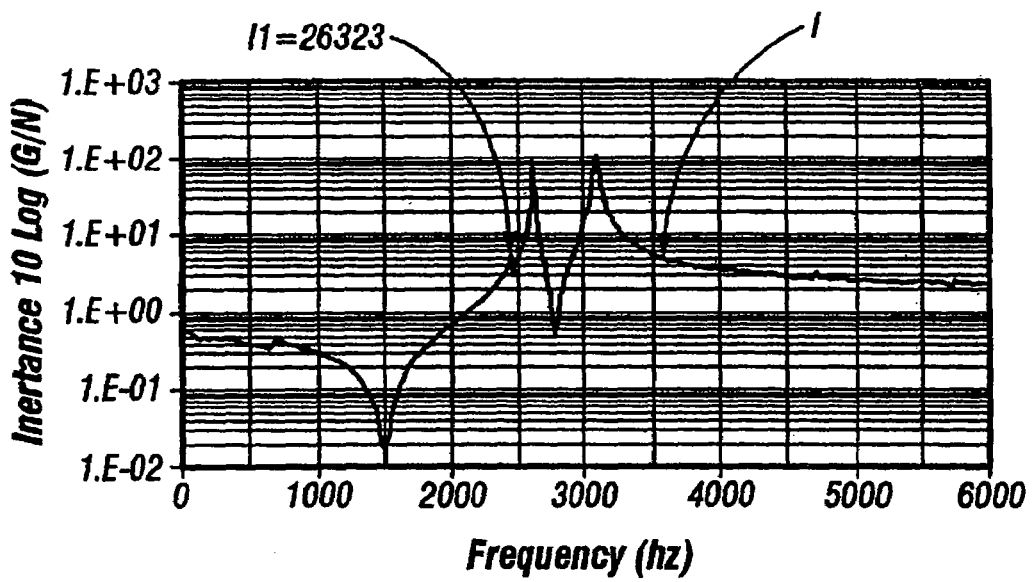
FIG. 17 is a graph of inertance versus frequency for the inventive club head.

FIG. 17 illustrates the inertance function of the inventive club head. The first primary resonant frequency is at 2632 Hz, and the COR of this inventive club was measured to be 0.824. The COR of the invention club is greater than the conventional club of FIG. 16, and therefore will provide greater ball rebound velocity.

Figure 18:
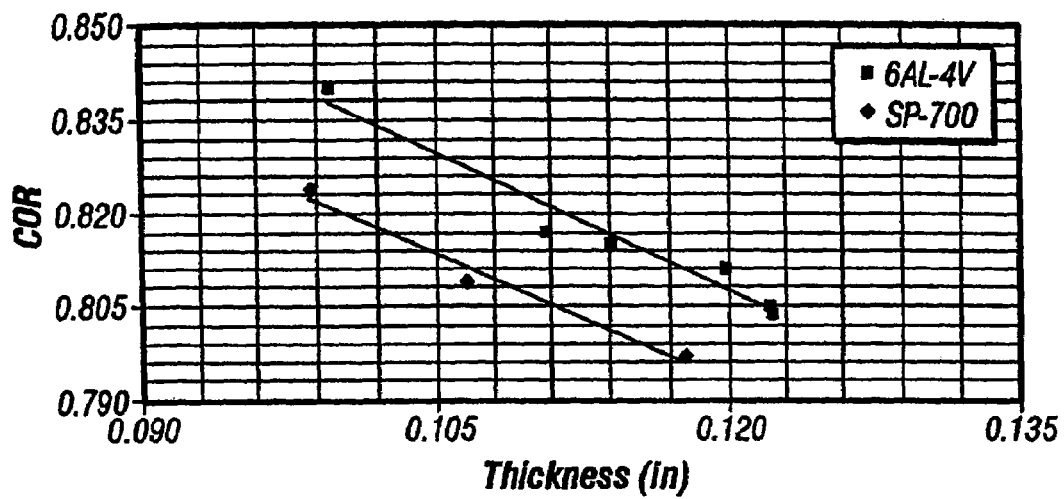
FIG. 18 is a graph of COR versus face thickness for two alternative titanium alloys.
Figure 19:
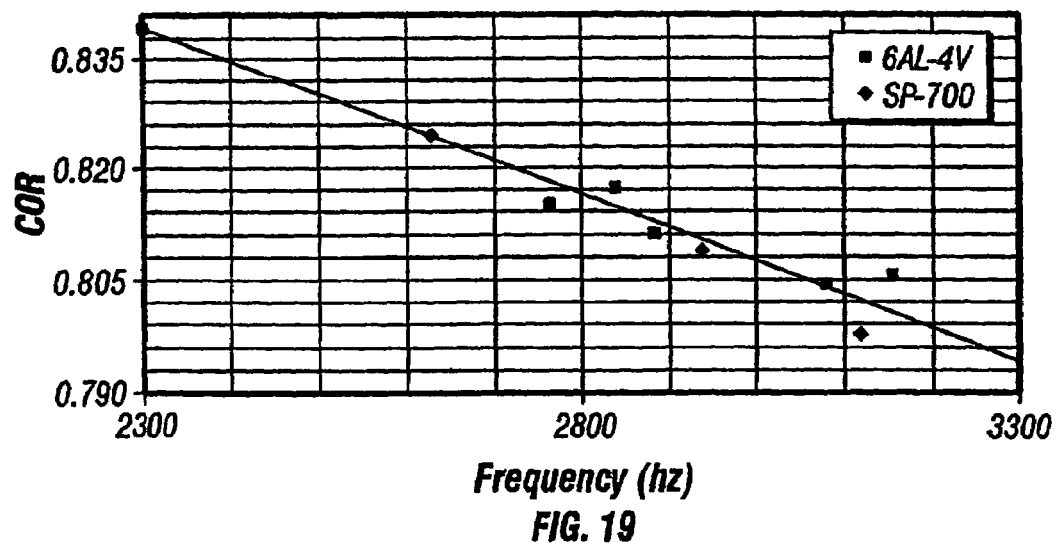
FIG. 19 is a graph of COR versus first resonant frequency for two alternative titanium alloys.

Several example club heads were produced with two commercially available titanium alloys 6AL-4V and SP700. The clubs were produced with a variety of uniform face thickness. FIG. 18 illustrates that as face thickness is reduced for a given titanium alloy the COR increases in a linear fashion. However, different titanium alloys with slightly different moduli have distinct trend lines and thickness alone is insufficient to predict COR. FIG. 19 illustrates a plot of COR versus first primary resonant frequency for the same set of club heads as those of FIG. 18. FIG. 18 illustrates that first primary resonant frequency is predictive of COR regardless of titanium alloy. The first primary resonant frequency of a club head may be used as a quality control factor to ensure compliance with USGA COR rules.

In accordance to another embodiment of the present invention, hitting face 16 is divided into two or more non-concentric regions having distinct flexural stiffness as illustrated in FIGS. 20–23. Club head 510 comprises toe 18, heel 20, sole plate 22, hosel 24, crown 28, and back portions similar to the other inventive clubs described above. Club head 510 further has a hitting face 516 that comprises an upper or crown face portion 520 and a lower or sole face portion 522. Club head 510 may also have an optional perimeter portion 540. Preferably, the flexural stiffness of the crown face portion 520 is different than the flexural stiffness of the sole face portion 522.

In accordance to one aspect, the flexural stiffness of crown face portion 520 is preferably about one half of the flexural stiffness of the sole face portion 522. In other words, the flexural stiffness of hitting face 516 varies and more specifically increases in the direction from crown 28 to sole 22. During an on-center or near center impact with a golf ball, as the hitting face deforms, crown face portion 520 deforms more than sole face portion 522 due to its lower flexural stiffness. This shift in the deformation causes a corresponding increase in launch angle of the golf ball, when compared to a similar golf club with a similar club loft angle but without the varying crown-to-sole flexural stiffness.

The increase in the launch angle of the golf ball achieved by the crown-to-sole flexural stiffness variation depends on a number of factors, including the location of the impacts on the hitting face and the flexural stiffness at the location of the impacts. Conversely, the launch angle of the golf ball can be reduced by reversing the crown-to-sole flexural stiffness variation, i.e., the flexural stiffness of the crown face portion 520 is higher than the flexural stiffness of the sole face portion 522. In this embodiment, the launch angle decreases because the sole face portion deforms more than the crown face portion.

Preferably, the flexural stiffness ($Et^3$) for the crown face portion 520 of hitting face 516 is between about 8,500 lb·in and about 60,000 lb·in, and the flexural stiffness of the sole face portion 522 is about twice (200%) of the flexural stiffness of the crown face portion 520 or less, such that the launch angle of the golf ball increases. On the other hand, the flexural stiffness of the sole face portion is about one-half (50%) of the flexural stiffness of the crown face portion or more such that the launch angle of the golf ball decreases. Suitable ratios of flexural stiffness between these portions include 4::1, 1::4, 2::3 or 3::2.

Figure 20:
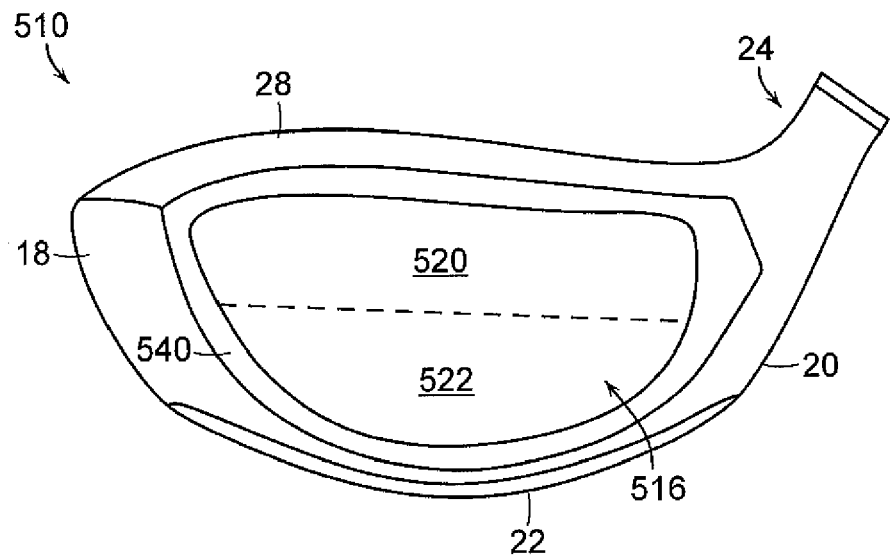
FIGS. 20–23 are front, elevational views of another embodiment in accordance to the present invention.
Figure 21:
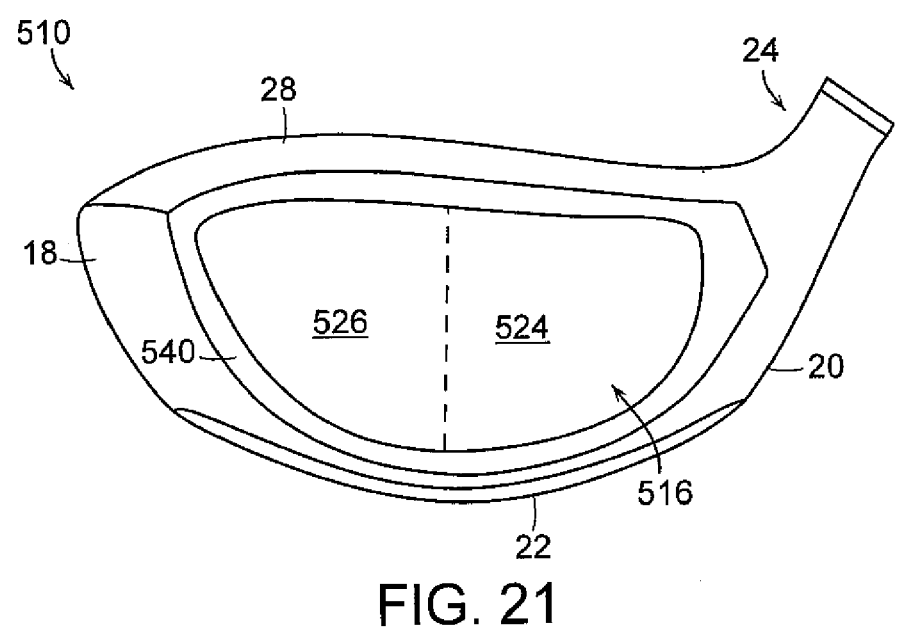

In accordance to another aspect of the present invention, as illustrated in FIG. 21 hitting face 516 of club head 510 comprises heel face portion 524 and toe face portion 526, such that the flexural stiffness of hitting face 516 varies in the heel-to-toe direction. Similar to the embodiment shown in FIG. 20, this hitting face also selectively and locally deforms to direct the angle of the golf ball in a desirable lateral direction. More specifically, for on-center or near-center impacts when the flexural stiffness of heel face portion 524 is lower than the flexural stiffness of toe face portion 526, the heel face portion deforms more to direct the angle of the ball more to the left of a right-handed golfer's body to compensate a tendency to slice or hook the ball to the right. On the other hand, when the flexural stiffness of the toe face portion 526 is lower than the flexural stiffness of the heel face portion 524, the toe face portion deforms more to direct the golf ball to the right of a right-handed golfer's body to compensate for a tendency to slice or hook the ball to the left.

Preferably, the flexural stiffness ($Et^3$) for the heel face portion 524 of hitting face 516 is between about 8,500 lb·in and about 60,000 lb·in, and the flexural stiffness of the toe face portion 526 is about twice (200%) of the flexural stiffness of the heel face portion 524 or less, such that the flight of the golf ball is directed to the left. On the other hand, the flexural stiffness of the toe face portion is about one-half (50%) of the flexural stiffness of the heel face portion or more such that the flight of the golf ball is directed to the right. Suitable ratios of flexural stiffness between these portions include 4::1, 1::4, 2::3 or 3::2.

Figure 22:
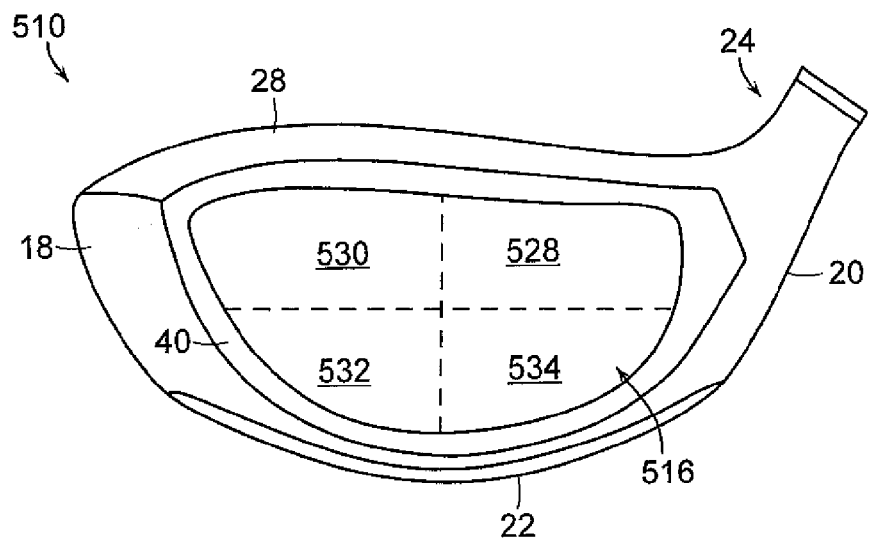

In accordance to another aspect of the present invention, the advantages of the hitting face shown in FIG. 20 and in FIG. 21 can be realized in a single hitting face, as illustrated in FIG. 22. Here, hitting face 516 comprises four portions: crown-heel portion 528, crown-toe portion 530, sole-toe portion 532 and sole-heel portion 534. The flexural stiffness of hitting face 516 can vary in both the crown-to-sole and heel-to-toe directions. The flexural stiffness can either increase or decrease in either direction. Hence, the advantages of altering the vertical launch angle and the lateral direction of the flight of a golf ball can be realized on a single golf club head.

Preferably, the flexural stiffness of the crown-heel portion 528 is between about 8,500 lb·in and about 60,000 lb·in. The flexural stiffness of the crown-toe portion 530 is preferably about 70% to about 130% of the flexural stiffness of crown-heel portion 528. The flexural stiffness of the sole-toe portion 532 is preferably about 50% to about 130% of the flexural stiffness of crown-heel portion 528. The flexural stiffness of the sole-heel portion 534 is preferably about 70% to about 200% of the flexural stiffness of crown-heel portion 528.

Figure 23:
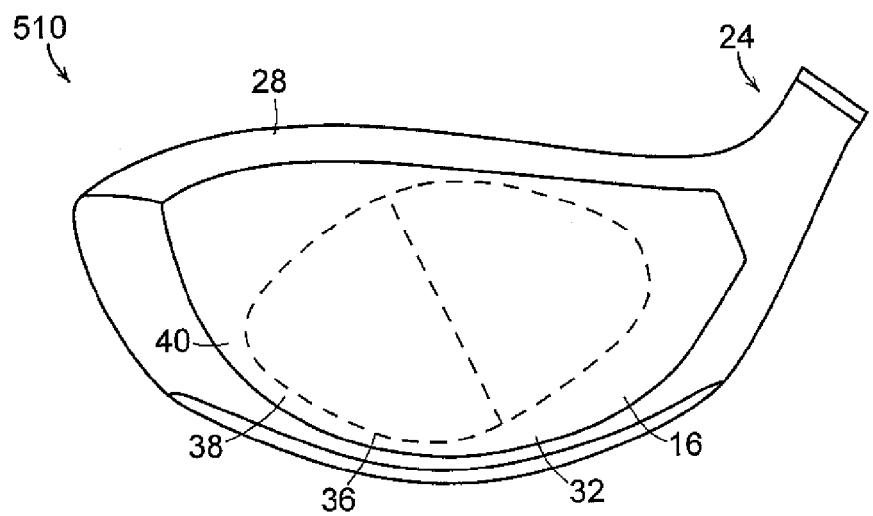

Alternatively, the hitting face 516 may comprise two or more non-concentric portions that make up any regular or irregular shape, such as the embodiment illustrated in FIG. 23. Furthermore, the boundaries between the non-concentric regions do not have to be substantially horizontal or substantially vertical.

Another readily apparent advantage of this embodiment is that it can reduce the manufacturing costs for golf clubs. The flexural stiffness of the hitting face can be altered in accordance to the present invention to achieve the effect of multiple lofts for a given head club design having a fixed loft angle. Tooling for a single mold with various face cavity inserts can produce a family of club heads having varying effective loft angles, albeit with a same exterior loft angle.

Figure 24:
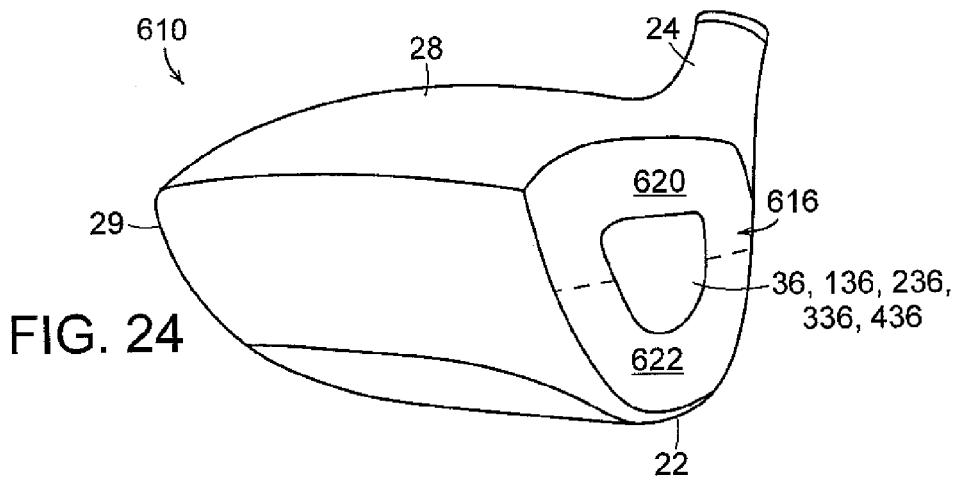
FIGS. 24–26 are perspective and front, elevational views of another embodiment in accordance to the present invention.
Figure 25:
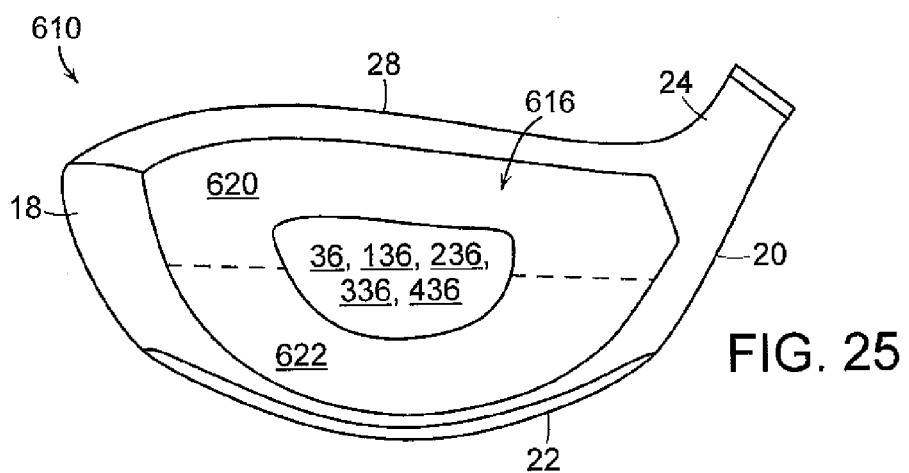

In accordance to another embodiment of the present invention, the advantages of the embodiments shown in FIGS. 1–19, i.e., having a rigid central portion 36, 136, 236, 336 or 446 and relatively flexible intermediate portion 38, 138, 238, 338 or 448, so that upon impact the intermediate portion deforms to provide high initial velocity while the central portion is substantially un-deformed so that the ball flies on-target ($FS_c/FS_I \geq 3$), among others, can be combined with the advantages of the embodiments shown in FIGS. 20–23, i.e., vertical and lateral control of the ball's flight. As illustrated in FIGS. 24–25, golf club head 610 comprises hitting face 616, which has a central portion 36, 136, 236, 336 or 436 surrounded by an intermediate portion comprising crown intermediate portion 620 and sole intermediate portion 622. Face 616 may also comprise an optional perimeter region (not shown). Preferably, the ratio of flexural stiffness between the central region and any portion of the intermediate region is greater than or equal to about 3.0, and more preferably between about 6.0 and about 12.0. In other words, this ratio between the central region and the crown intermediate portion 620 and between the central region and the sole intermediate portion 622 is greater than or equal to about 3.0, and more preferably between about 6.0 and about 12.0.

In this embodiment, preferably the flexural stiffness of the two intermediate portions 620 and 622 are different. Crown intermediate portion 620 may have a lower flexural stiffness than sole intermediate portion 622, or vice versa, depending on the desired launch angle of the ball. In one non-limiting example, the ratio of flexural stiffness between the central region and the crown intermediate portion 620 is about 9.0, while the same ratio between the central region and the sole intermediate portion is about 6.0 to control the launch angle of the golf ball.

Figure 26:
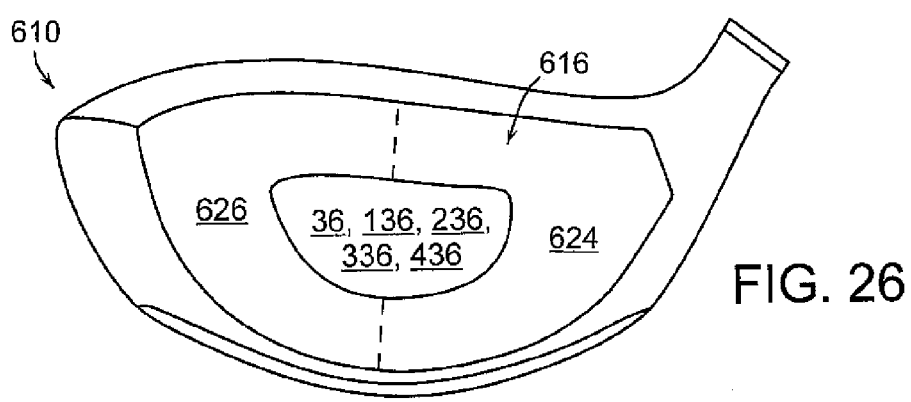

On the other hand, to control the lateral launch angle of the golf ball while maintaining the high initial velocity produced by the ($FS_c/FS_1 \geq 3$) flexural stiffness ratio, hitting face 616 may comprise central region 36, 136, 236, 336 or 436 and an intermediate region comprising heel intermediate portion 624 and toe intermediate portion 626, as shown in FIG. 26. Preferably, the ratio of flexural stiffness between the central region and any portion of the intermediate region is greater than or equal to about 3.0, and more preferably between about 6.0 and about 12.0. In other words, this ratio between the central region and the heel intermediate portion 620 and between the central region and the toe intermediate portion 622 is greater than or equal to about 3.0, and more preferably between about 6.0 and about 12.0, or greater than 12.0.

In this embodiment, preferably the flexural stiffness of the two intermediate portions 624 and 626 are different. Heel intermediate portion 620 may have a lower flexural stiffness than toe intermediate portion 622, or vice versa, depending on the desired lateral angle of the ball. In one non-limiting example, the ratio of flexural stiffness between the central region and the heel intermediate portion 620 is about 9.0, while the same ratio between the central region and the toe intermediate portion is about 6.0 to control the lateral angle of the golf ball.

In accordance to another aspect of the invention, hitting face 616 may comprise a central region, as discussed above, and an intermediate region comprising four portions: crown-heel intermediate portion, crown-toe intermediate portion, sole-toe intermediate portion and sole-heel intermediate portion, similar to the embodiment shown in FIG. 22. Each intermediate portion preferably has different flexural stiffness to vary the launch and lateral angle of the golf ball. Furthermore, the ratio of flexural stiffness between the central region and each of the intermediate portions is greater than or equal to about 3.0, and more preferably between about 6.0 and about 12.0.

While various descriptions of the present invention are described above, it should be understood that the various features of each embodiment can be used alone or in any combination thereof. Therefore, this invention is not to be limited to only the specifically preferred embodiments depicted herein. Further, it should be understood that variations and modifications within the spirit and scope of the invention may occur to those skilled in the art to which the invention pertains. For example, the face and/or individual portions can have thickness variations in a step-wise or continuous fashion. Other modifications include a perimeter portion that has a thickness that is greater than or less than the adjacent, intermediate portion. In addition, the shapes of the central, intermediate, and perimeter portions are not limited to those disclosed herein. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A golf club head adapted for attachment to a shaft and having a hitting face, wherein the hitting face comprises a directional control portion, said directional controlled portion comprises two or more non-concentric zones having different flexural stiffness, such that when the hitting face impacts a golf ball the zones exhibit different degrees of deformation to selectively control the direction of the flight of the golf ball, wherein the hitting face further comprises a central portion disposed within the directional control portion such that the central portion contains a geometric center of the hitting face and wherein the flexural stiffness of the central portion is at least about three times greater than the flexural stiffness of the directional control portion.

2. The golf club head of claim 1, wherein the flexural stiffness of the central portion is at least about six times greater than the flexural stiffness of the directional control portion.

3. The golf club head of claim 2, wherein the flexural stiffness of the central portion is at least about twelve times greater than the flexural stiffness of the directional control portion.

4. The golf club head of claim 1, further comprising a perimeter portion disposed around the directional control portion, wherein the flexural stiffness of the perimeter portion is at least about two times greater than the flexural stiffness of the directional control portion.

5. The golf club head of claim 1, wherein the hitting face comprises a laminate material.

6. The golf club head of claim 1, wherein the directional control portion comprises an upper too zone and a lower heel zone.

7. The golf club head of claim 1, wherein the directional control portion comprises a lateral heel zone and a lateral toe zone.

8. The golf club head of claim 1, wherein the directional control portion comprises four zones, an wherein the zones are delineated by a vertical center line and a horizontal center line of the hitting face.

9. The golf club head of claim 1, wherein the flexural stiffness of a first zone of said two or more zones is between about 8,500 lb·in to about 60,000 lb·in.

10. The golf club head of claim 9, wherein the flexural stiffness of a second zone of said two or more zones is about 0.5 times about two times the flexural stiffness of the first zone.

11. The golf club head of claim 9, wherein the flexural stiffness of a third zone of said two or more zones is about 0.7 times to about 1.3 times the flexural stiffness of the first zone.

12. The golf club head of claim 9, wherein the flexural stiffness of a fourth zone of said two or more zones is about 0.7 times to about two times the flexural stiffness of the first zone.

* * * * *